(12) United States Patent
Jackson

(10) Patent No.: US 8,060,960 B2
(45) Date of Patent: Nov. 22, 2011

(54) PATIENT POSITIONING SUPPORT STRUCTURE

(76) Inventor: Roger P. Jackson, Prairie Village, KS (US)

( * ) Notice: Subject to any disclaimer, the term of this patent is extended or adjusted under 35 U.S.C. 154(b) by 0 days.

(21) Appl. No.: 12/460,702

(22) Filed: Jul. 23, 2009

(65) Prior Publication Data

US 2009/0282614 A1  Nov. 19, 2009

Related U.S. Application Data

(63) Continuation of application No. 11/788,513, filed on Apr. 20, 2007, now Pat. No. 7,565,708, which is a continuation-in-part of application No. 11/159,494, filed on Jun. 23, 2005, now Pat. No. 7,343,635, and a continuation-in-part of application No. 11/062,775, filed on Feb. 22, 2005, now Pat. No. 7,152,261.

(60) Provisional application No. 60/798,288, filed on May 5, 2006.

(51) Int. Cl.
A61G 13/04 (2006.01)
A61G 13/08 (2006.01)

(52) U.S. Cl. .................. 5/611; 5/610; 5/607; 5/613

(58) Field of Classification Search ............. 5/607, 608, 5/610, 611, 613, 617, 618
See application file for complete search history.

(56) References Cited

U.S. PATENT DOCUMENTS

| | | |
|---|---|---|
| 1,938,006 A | 12/1933 | Blanchard |
| 2,261,297 A | 11/1941 | Frederick |
| 2,636,793 A | 4/1953 | Meyer |
| 3,281,141 A | 10/1966 | Smiley et al. |
| 3,584,321 A | 6/1971 | Buchanan |
| 3,599,964 A | 8/1971 | Magni |
| 3,766,384 A | 10/1973 | Anderson |
| 3,814,414 A | 6/1974 | Chapa |
| 4,101,120 A | 7/1978 | Seshima |
| 4,131,802 A | 12/1978 | Braden et al. |
| 4,144,880 A | 3/1979 | Daniels |
| 4,148,472 A | 4/1979 | Rais et al. |
| 4,175,550 A | 11/1979 | Leininger et al. |
| 4,186,917 A | 2/1980 | Rais et al. |
| 4,503,844 A | 3/1985 | Siczek |
| 4,552,346 A | 11/1985 | Schnelle et al. |
| 4,712,781 A | 12/1987 | Watanabe |
| 4,763,643 A | 8/1988 | Vrzalik |

(Continued)

FOREIGN PATENT DOCUMENTS

WO  WO 00/62731  10/2000

OTHER PUBLICATIONS

Brochure of Smith & Nephew on Spinal Positioning System, 2003, 2004.

(Continued)

*Primary Examiner* — Michael Trettel
(74) *Attorney, Agent, or Firm* — John C. McMahon

(57) ABSTRACT

A patient support system includes independently adjustable end columns supporting a centrally hinged, jointed or breaking patient support structure. At least one column includes a powered rotation assembly. The patient support includes at least two sections. A coordinated drive system provides for both upwardly and downwardly breaking or jointed orientations of the two sections in various inclined and tilted positions. Cable, cantilevered and pull-rod systems are included.

52 Claims, 29 Drawing Sheets

U.S. PATENT DOCUMENTS

| | | |
|---|---|---|
| 4,872,657 A | 10/1989 | Lussi |
| 5,088,706 A | 2/1992 | Jackson |
| 5,131,106 A | 7/1992 | Jackson |
| 5,210,888 A | 5/1993 | Canfield |
| 5,239,716 A | 8/1993 | Fisk |
| 5,393,018 A | 2/1995 | Roth et al. |
| 5,444,882 A | 8/1995 | Andrews et al. |
| 5,588,705 A | 12/1996 | Chang |
| 5,658,315 A * | 8/1997 | Lamb et al. .................. 606/241 |
| 5,794,286 A | 8/1998 | Scott et al. |
| 6,260,220 B1 | 7/2001 | Lamb et al. |
| 6,295,671 B1 | 10/2001 | Reesby et al. |
| 6,438,777 B1 | 8/2002 | Bender |
| 6,505,365 B1 | 1/2003 | Hanson et al. |
| 6,526,610 B1 | 3/2003 | Hand et al. |
| 6,634,043 B2 | 10/2003 | Lamb et al. |
| 6,638,299 B2 | 10/2003 | Cox |
| 6,681,423 B2 | 1/2004 | Zachrisson |
| 7,565,708 B2 * | 7/2009 | Jackson ........................... 5/611 |
| 2004/0133983 A1 | 7/2004 | Newkirk et al. |
| 2008/0000028 A1 | 1/2008 | Lemire et al. |

OTHER PUBLICATIONS

Brochure of OSI on Modular Table System 90D, pp. 1-15, date of first publication: Unknow.

Pages from website http://www.schaerermayfieldusa.com, pp. 1-5, date of first publication: Unknown.

* cited by examiner

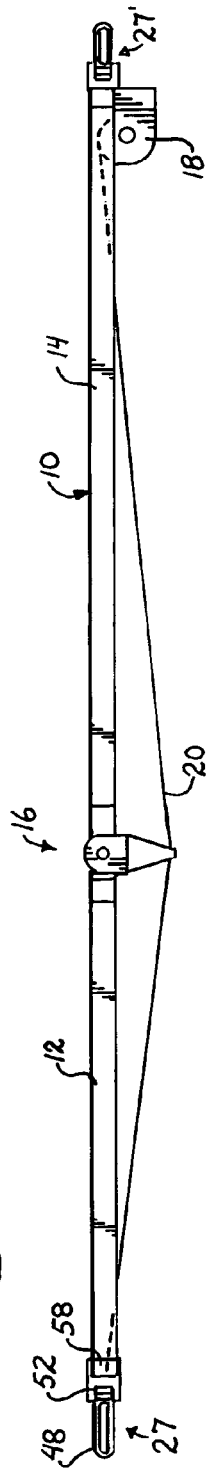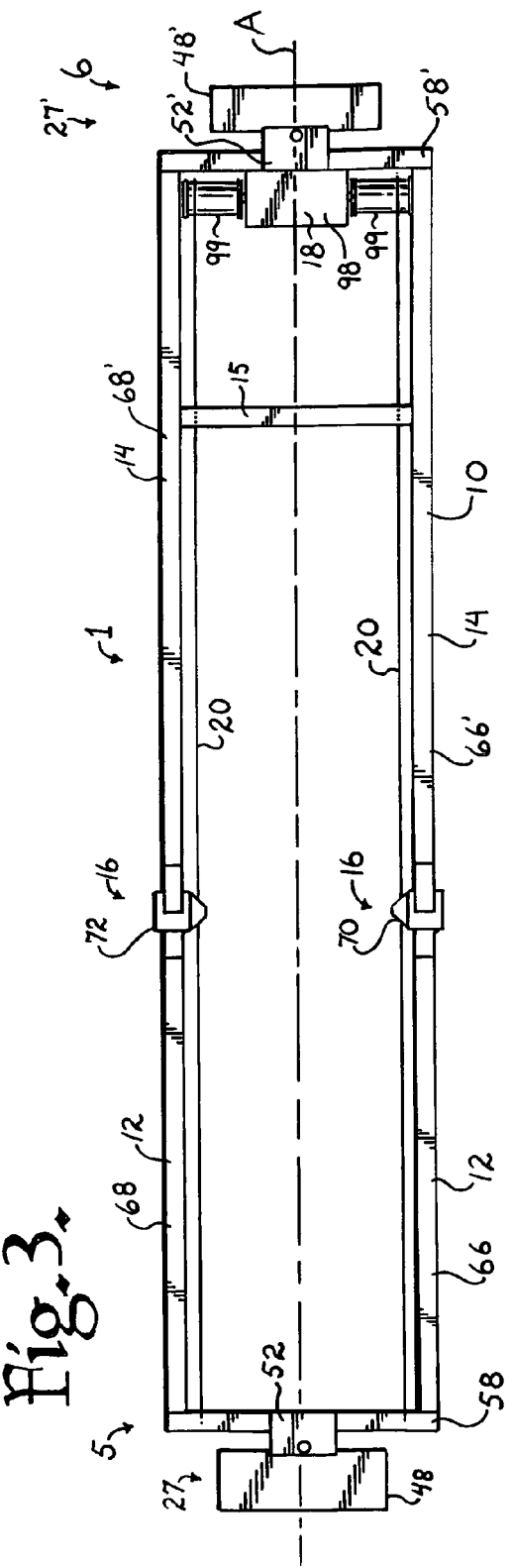

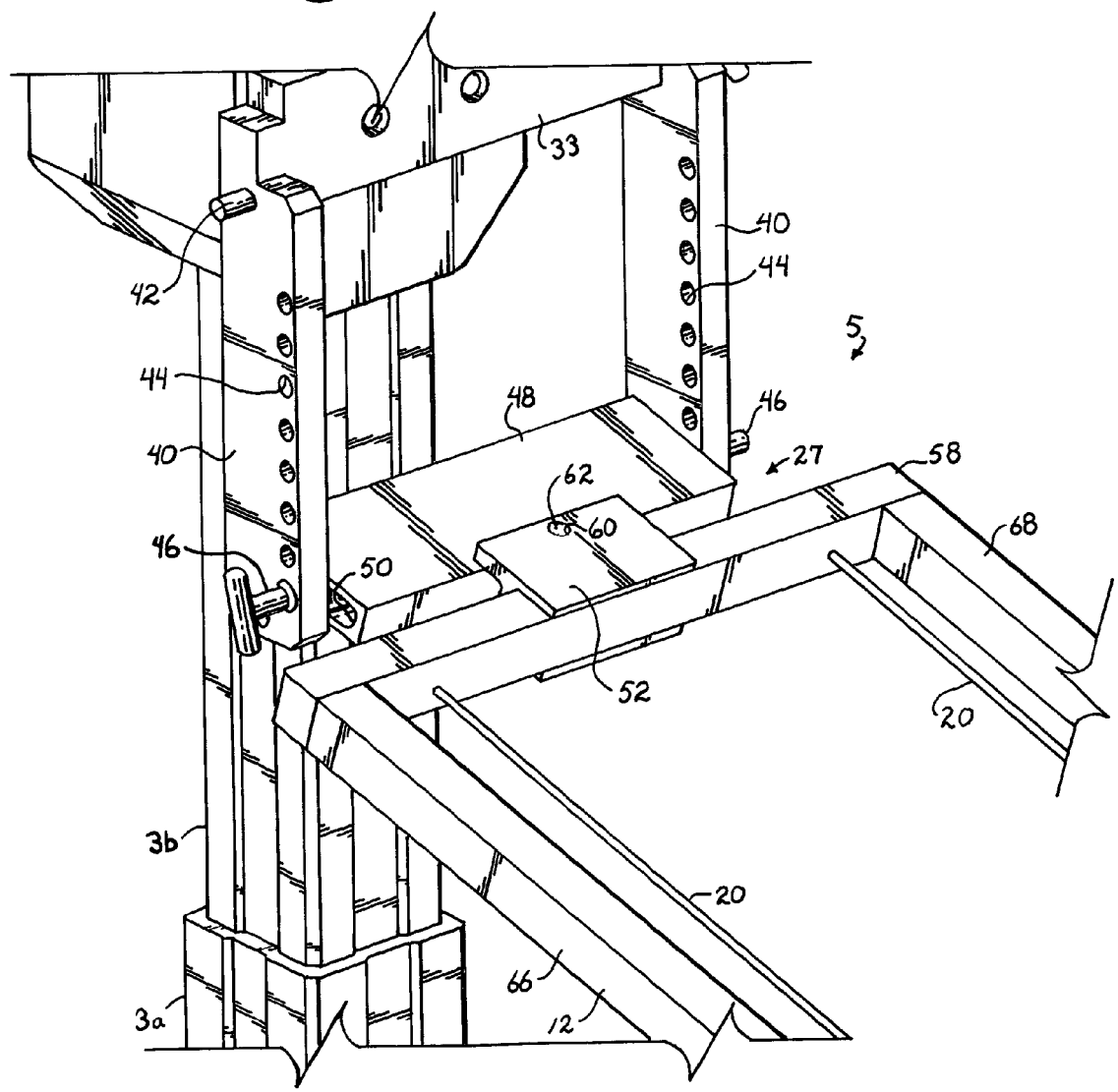

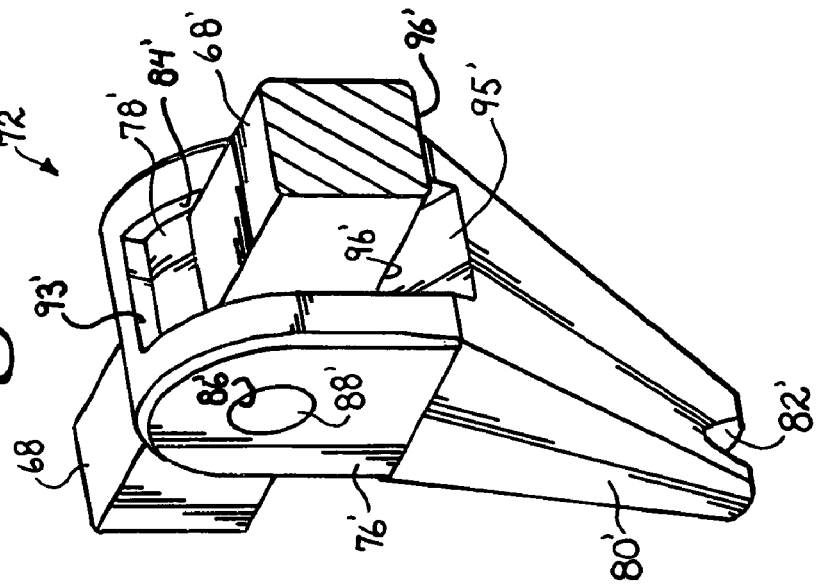
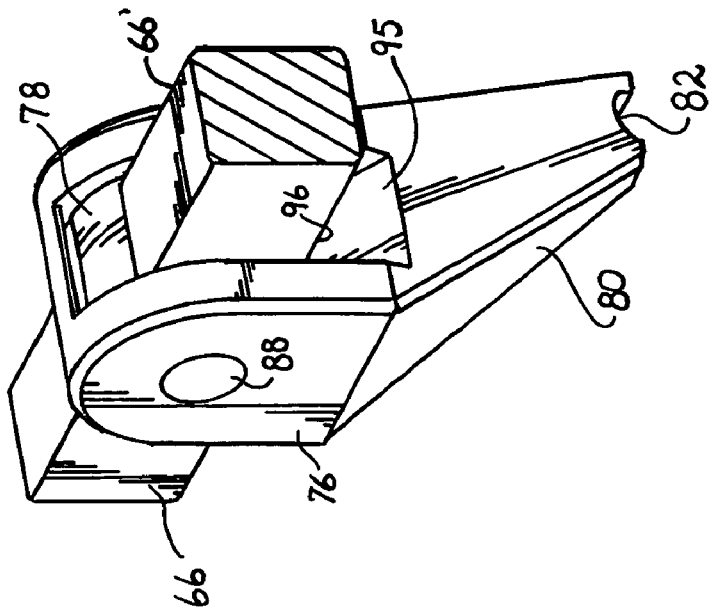

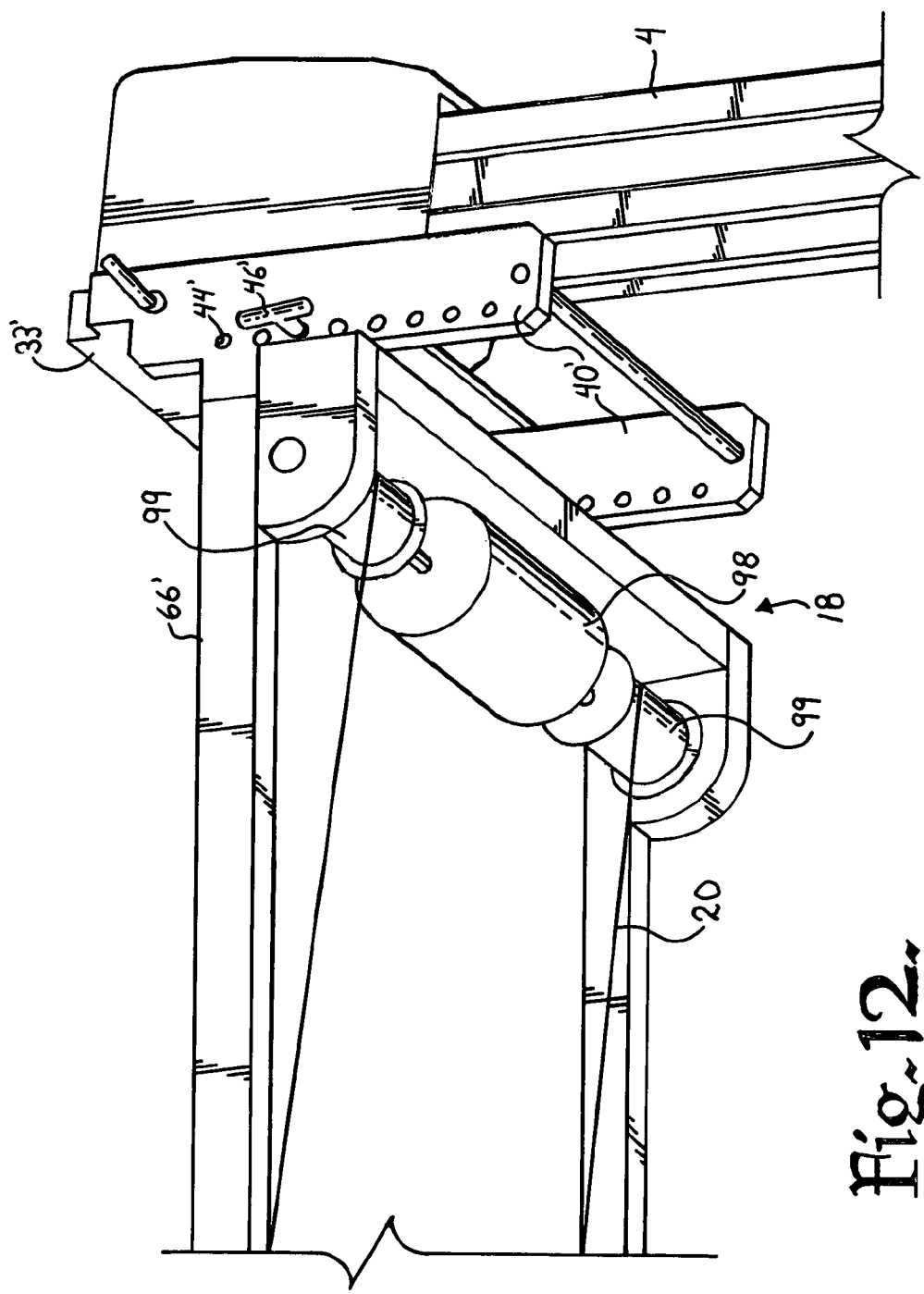

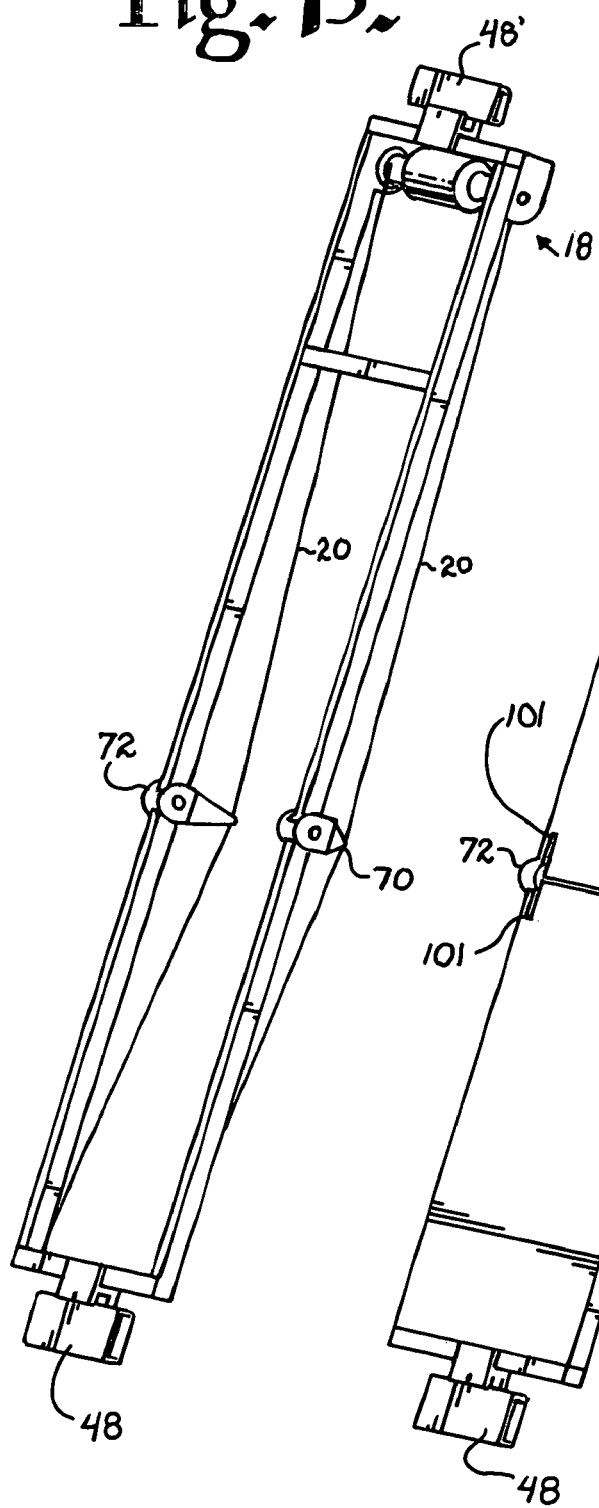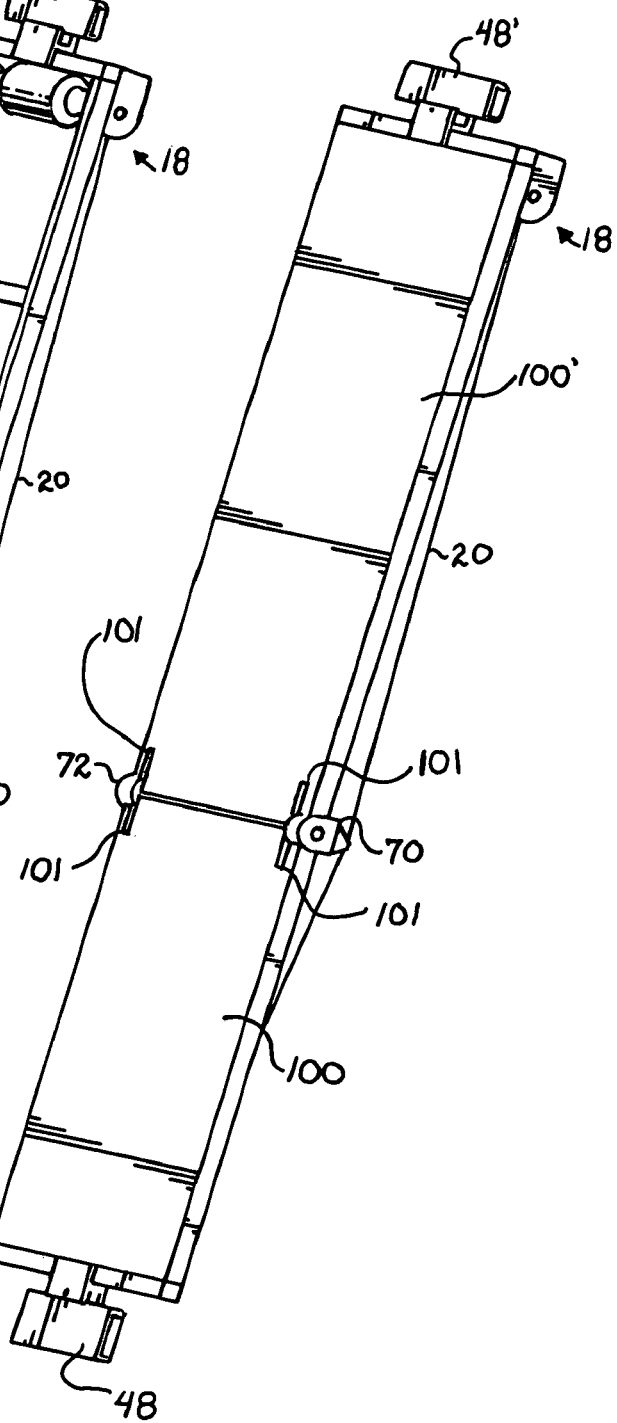

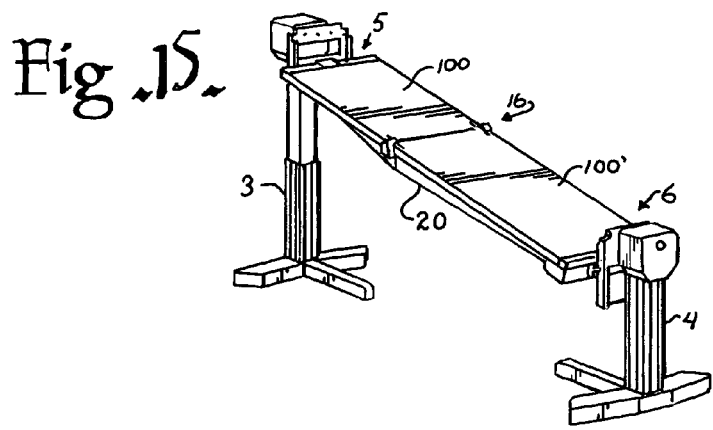
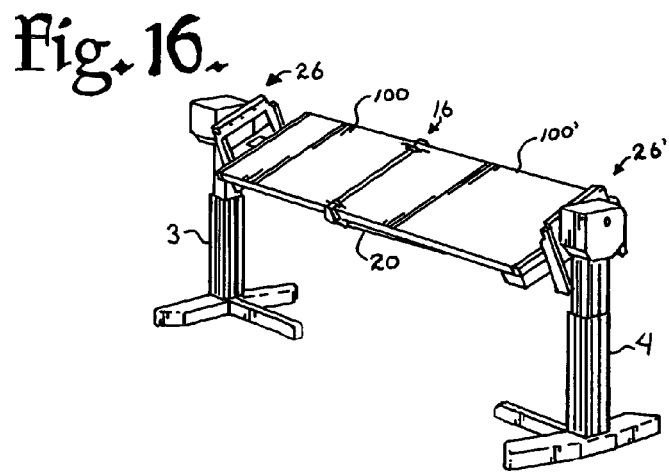
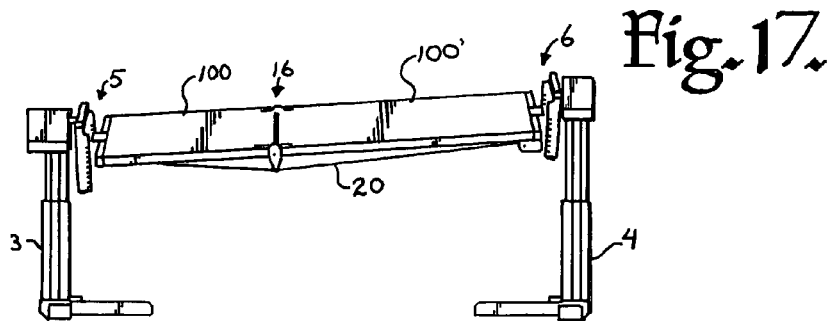

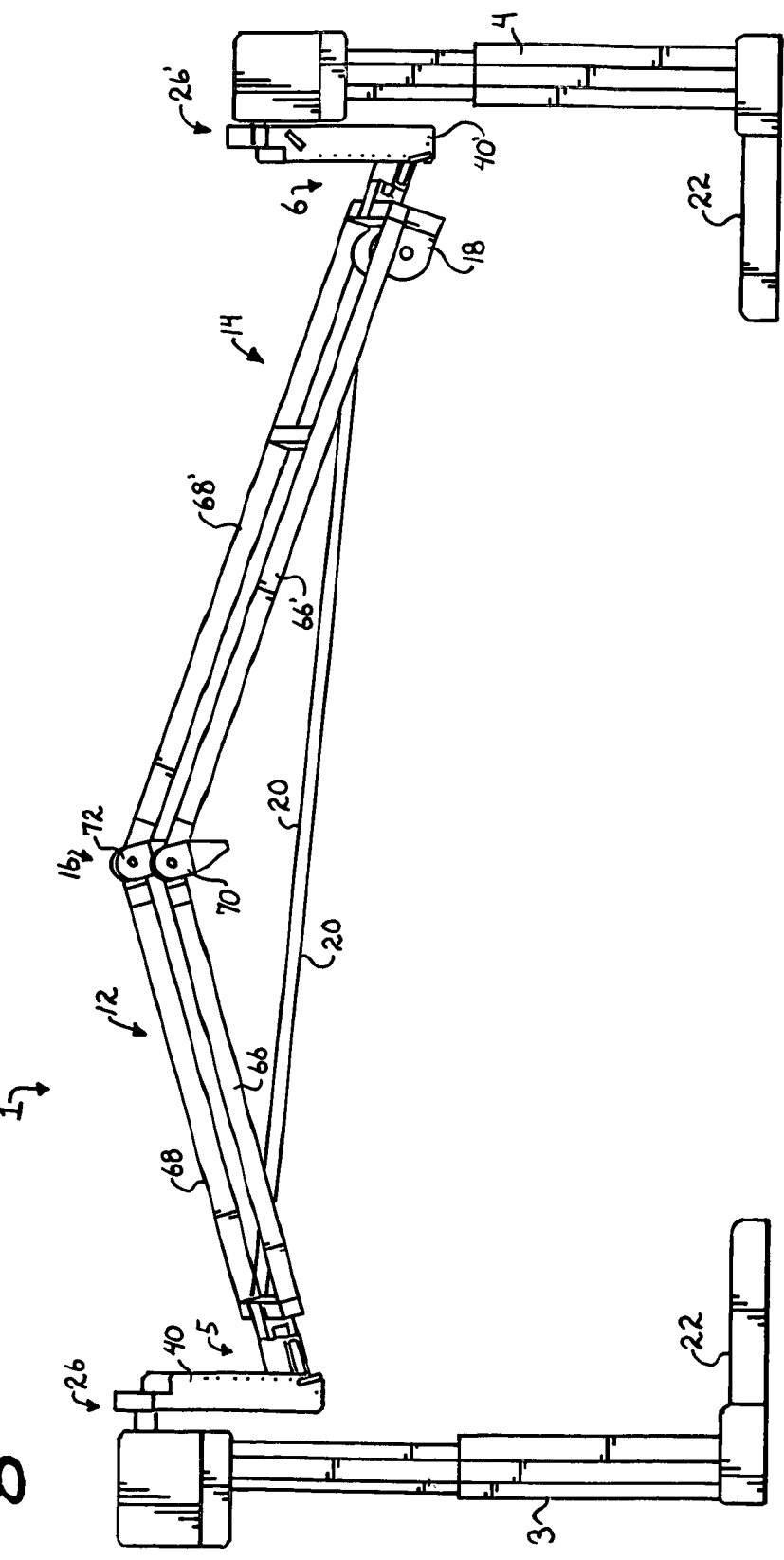

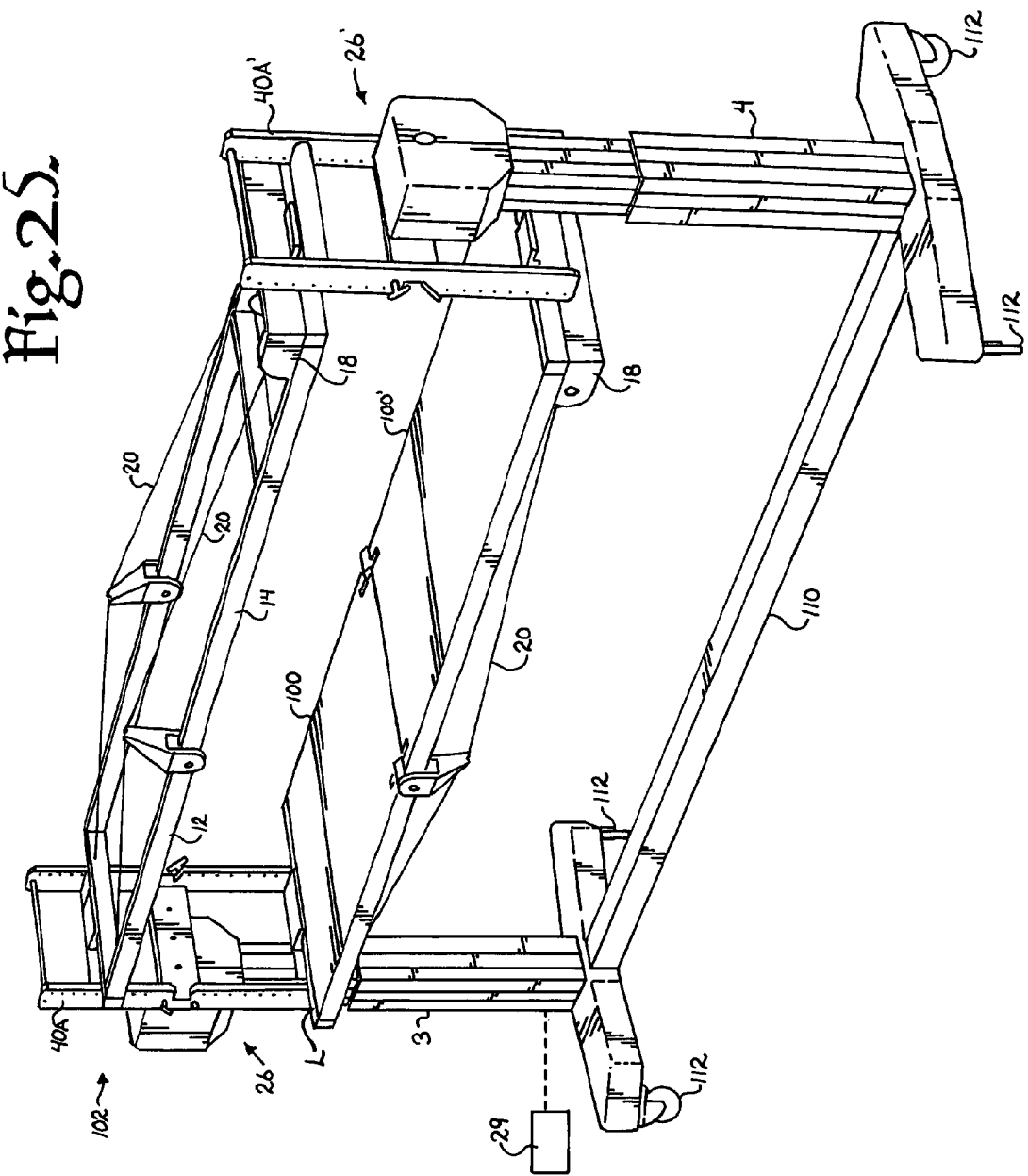

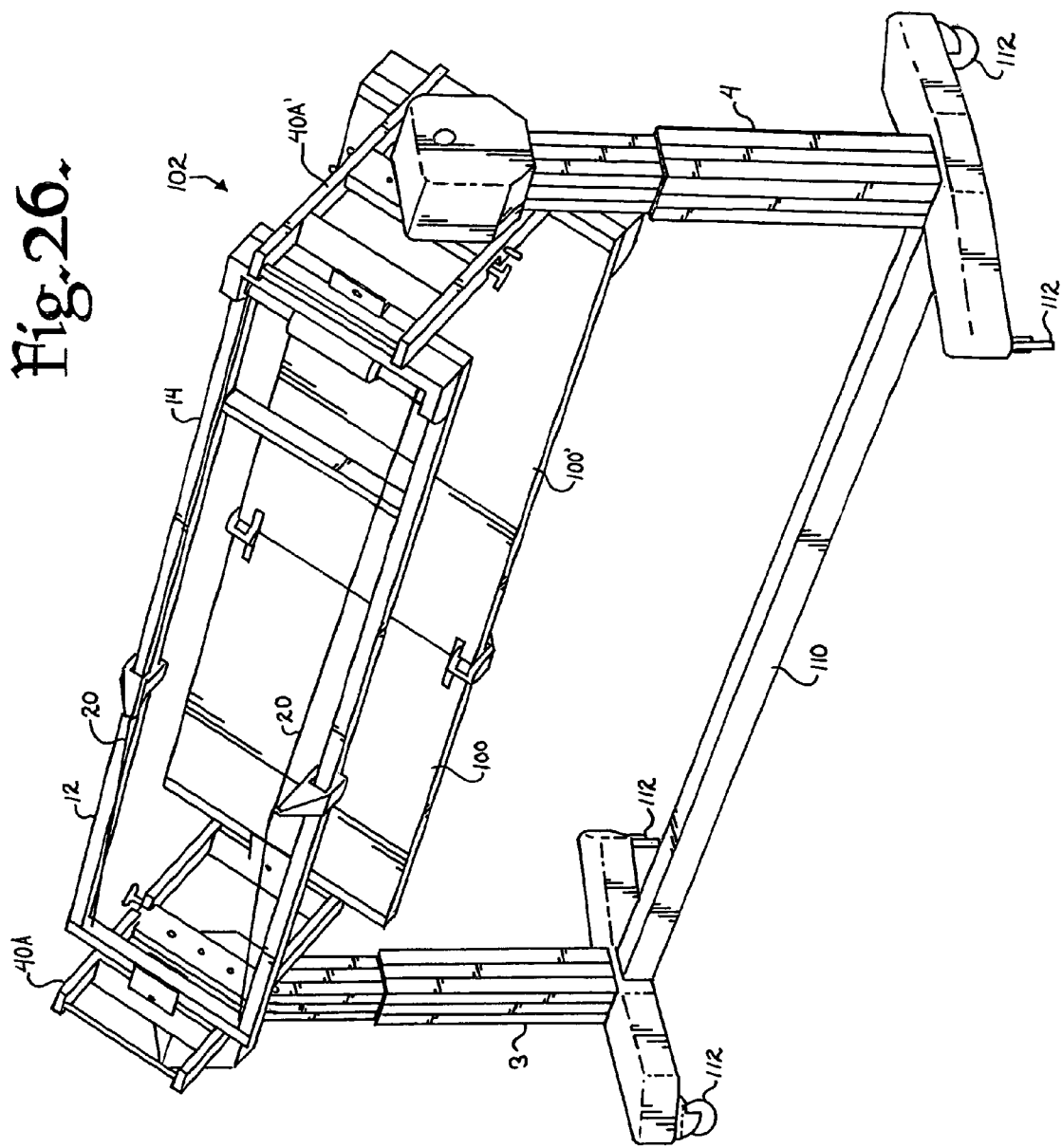

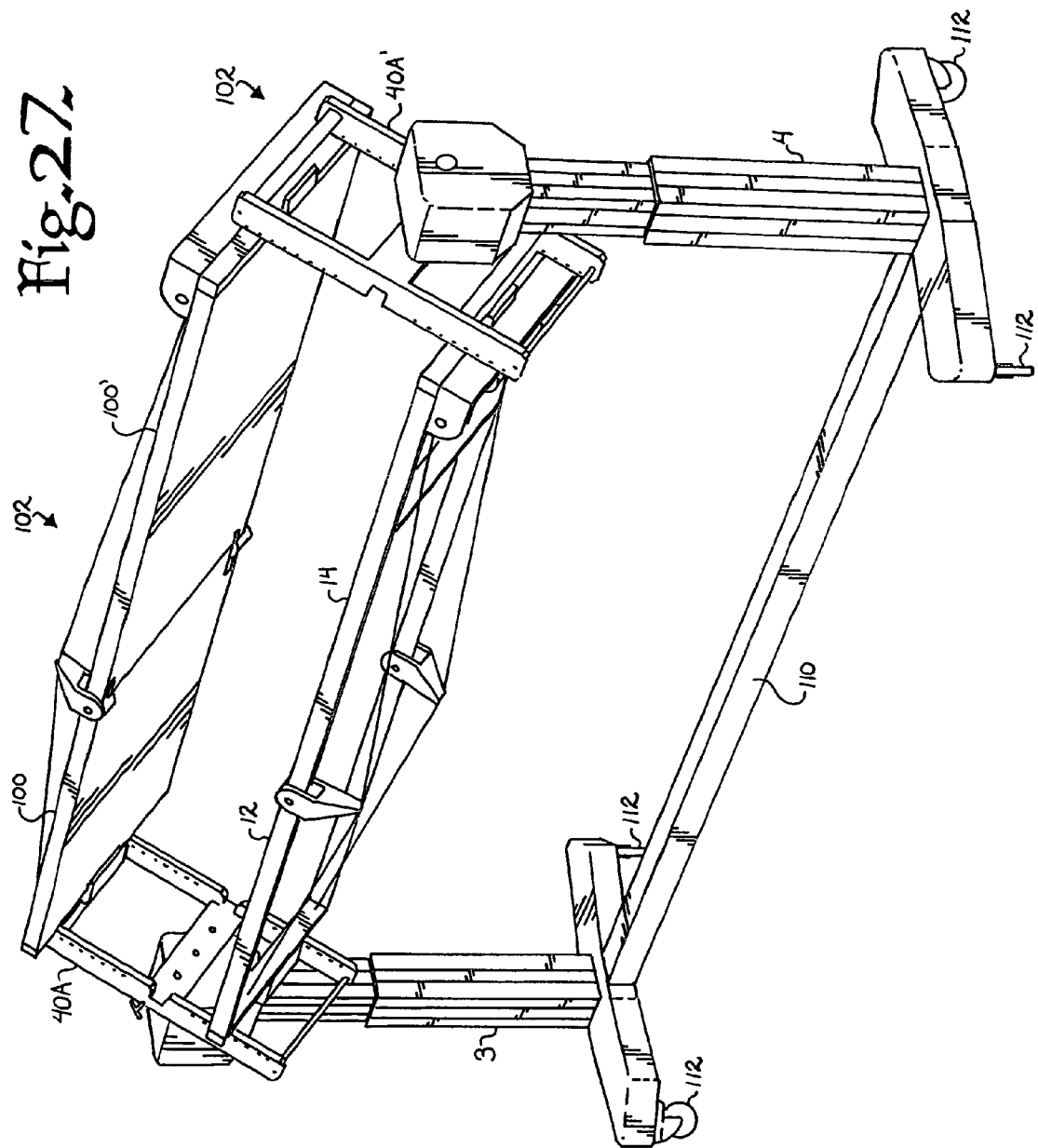

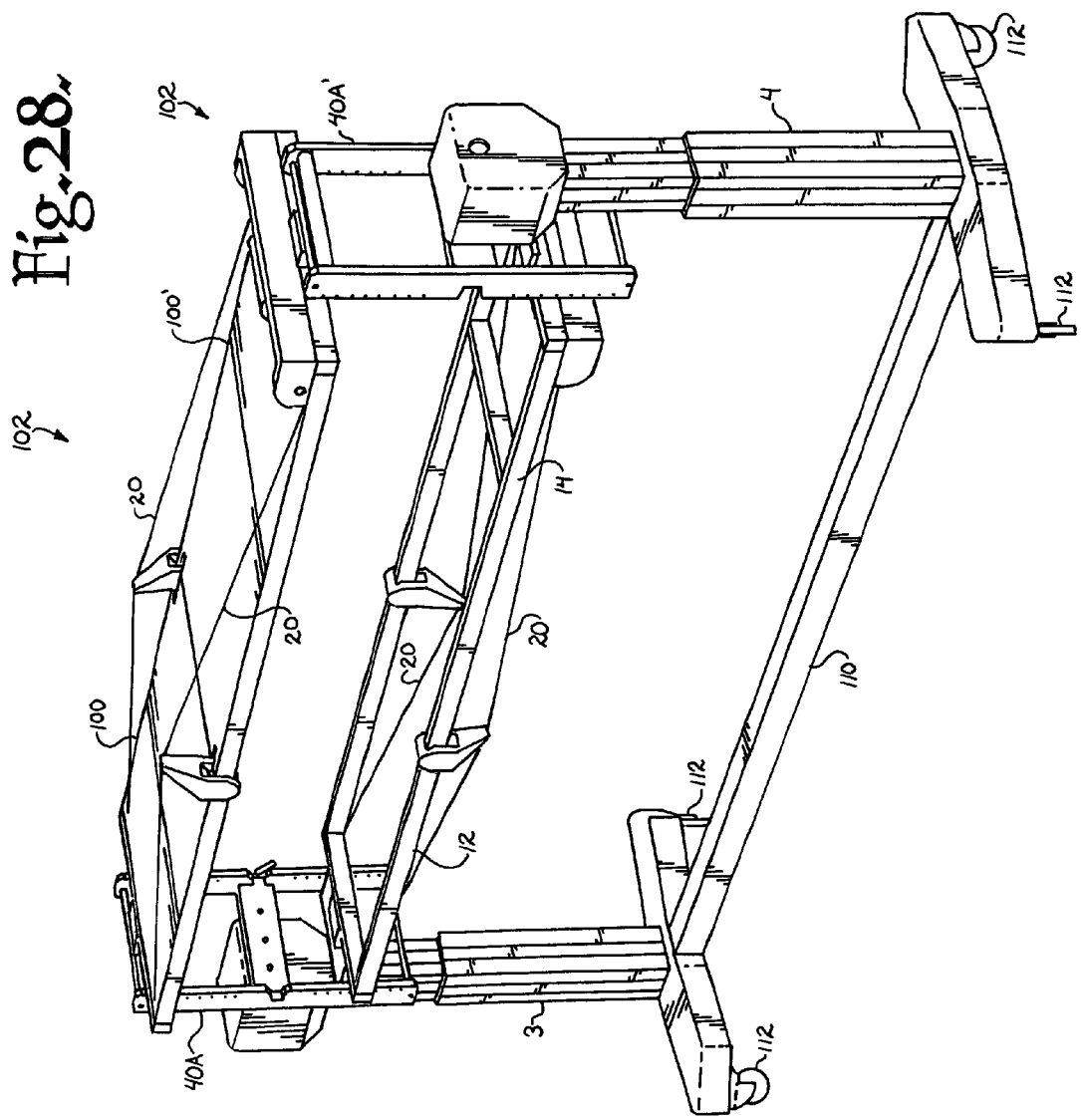

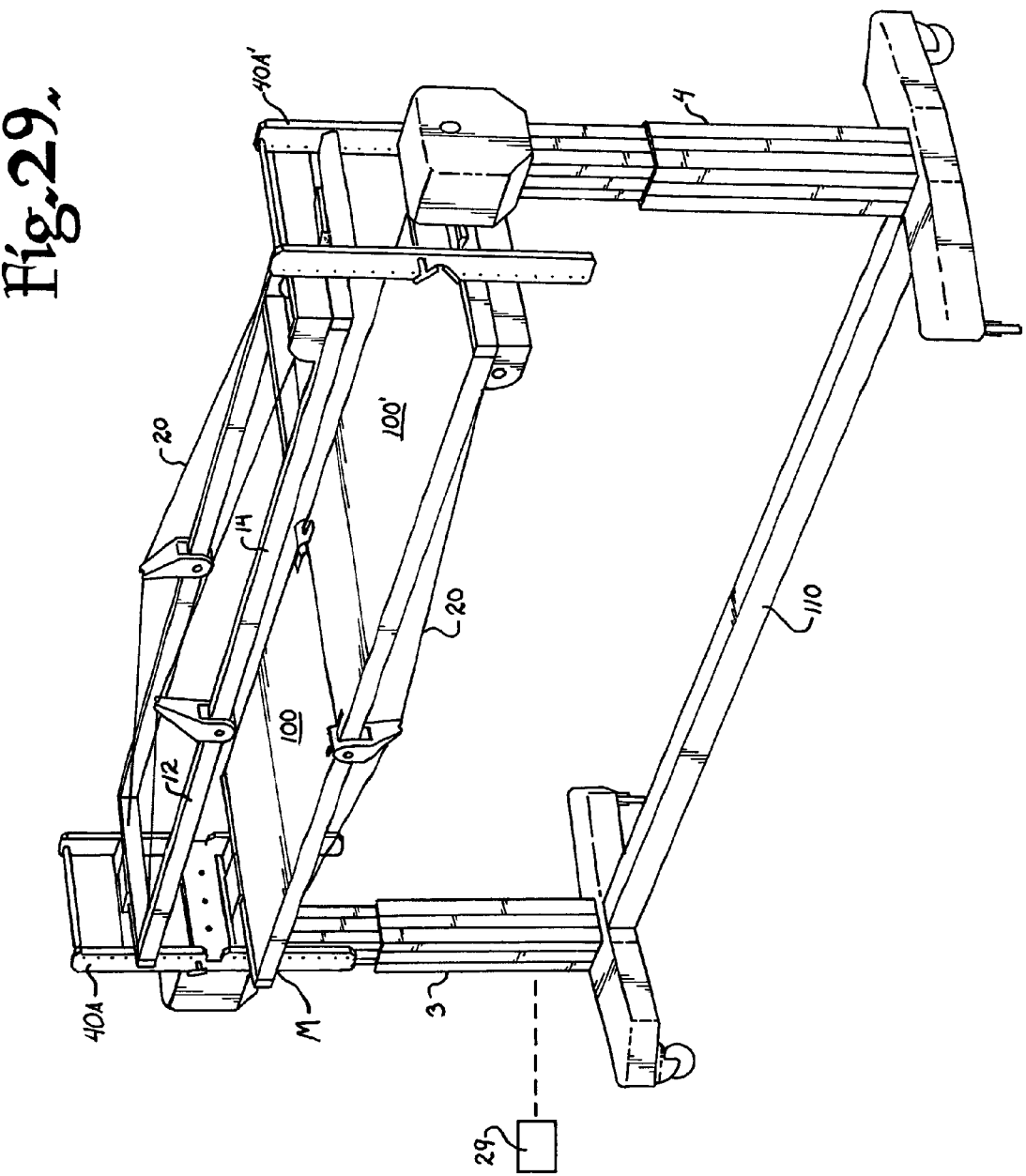

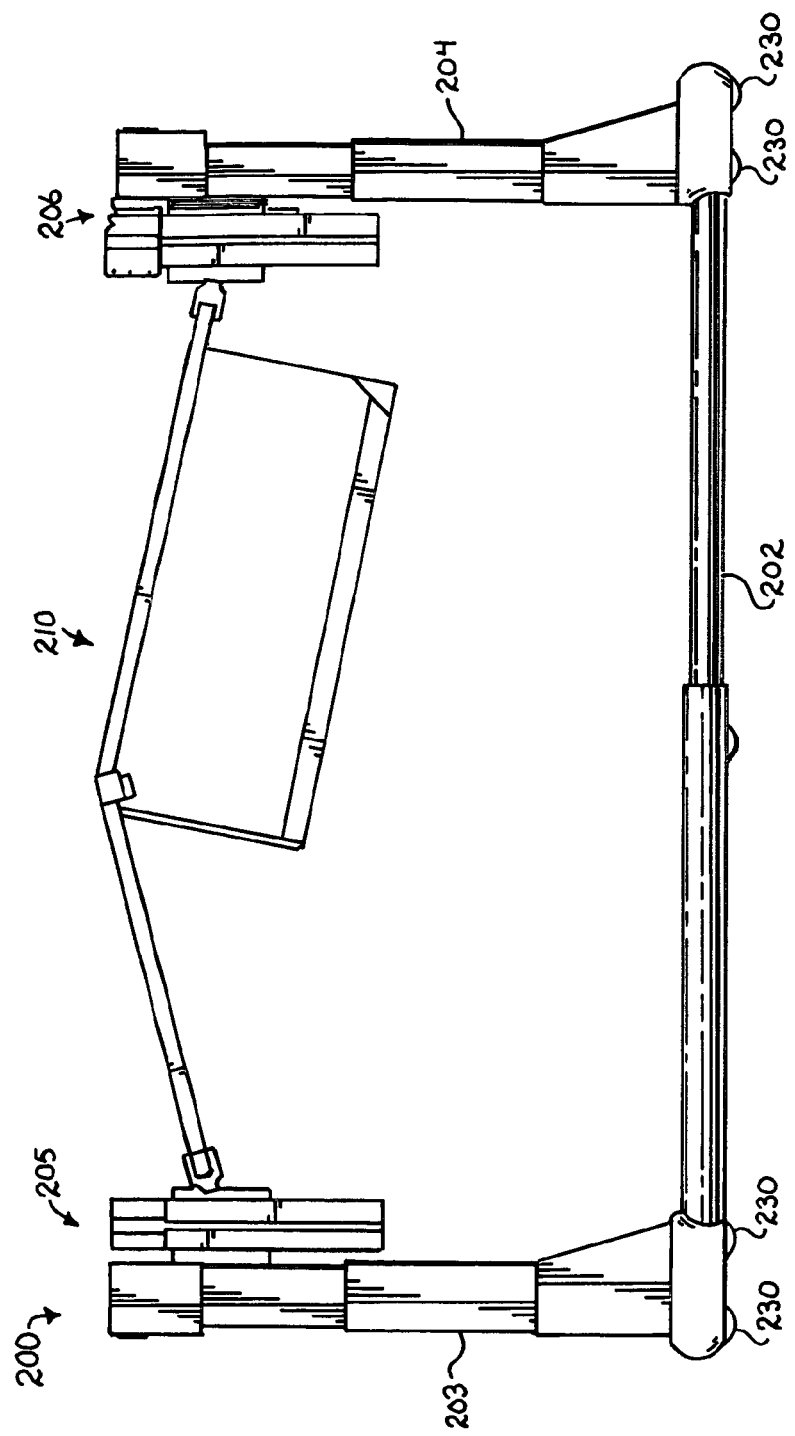

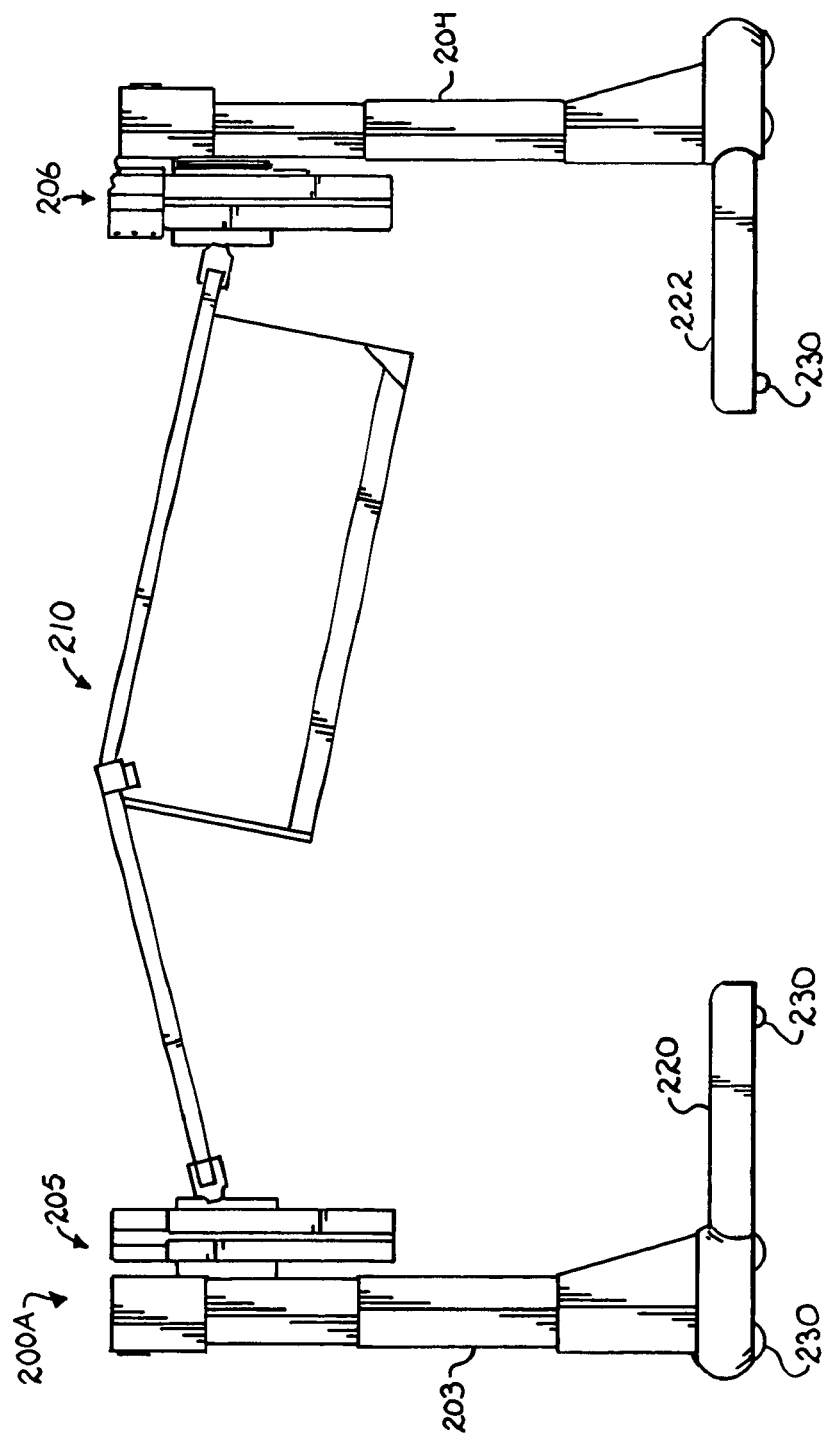

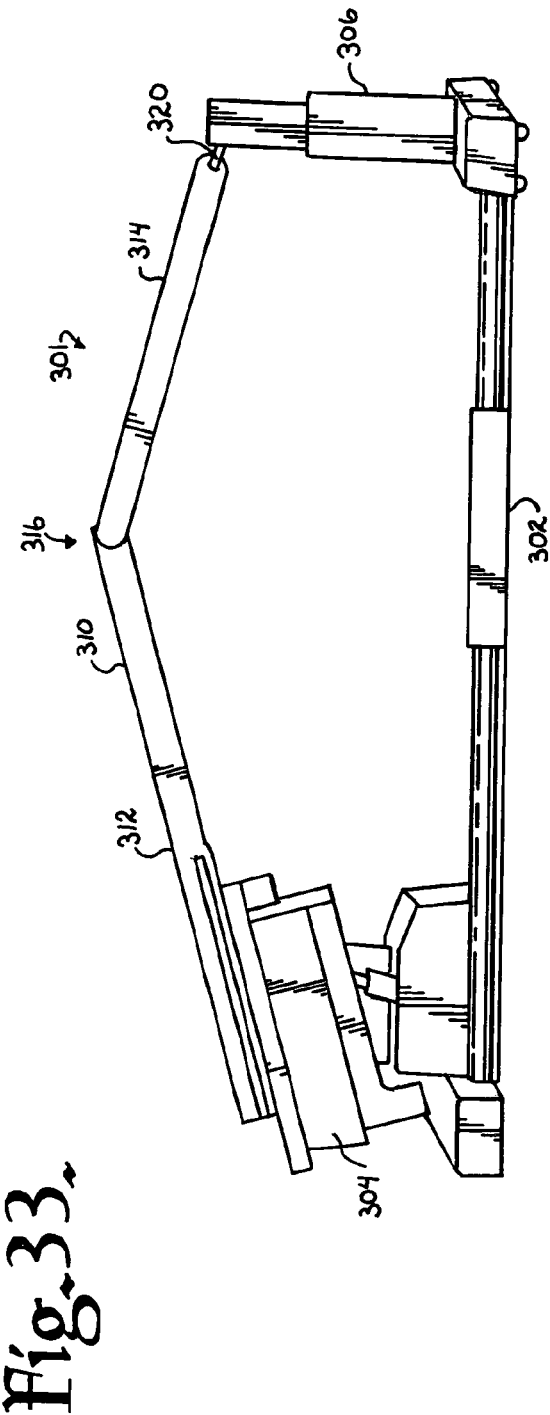
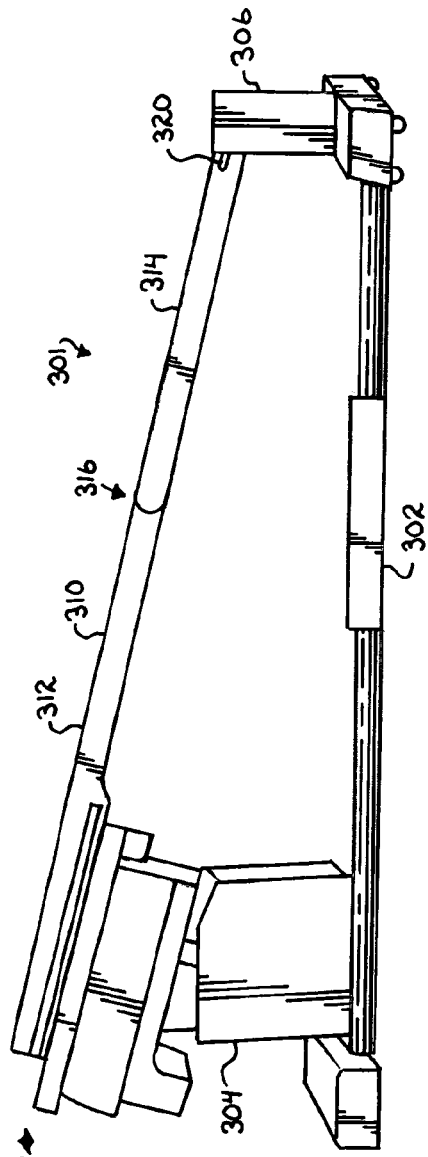
Fig-33.
Fig-32.

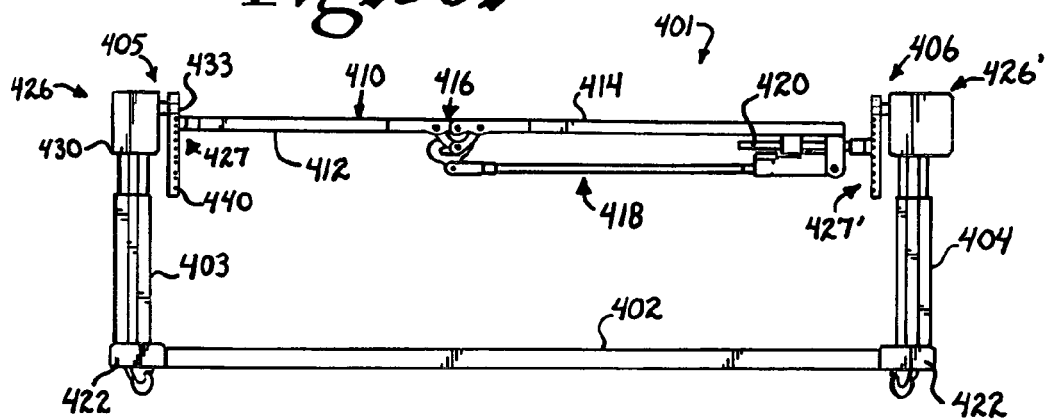
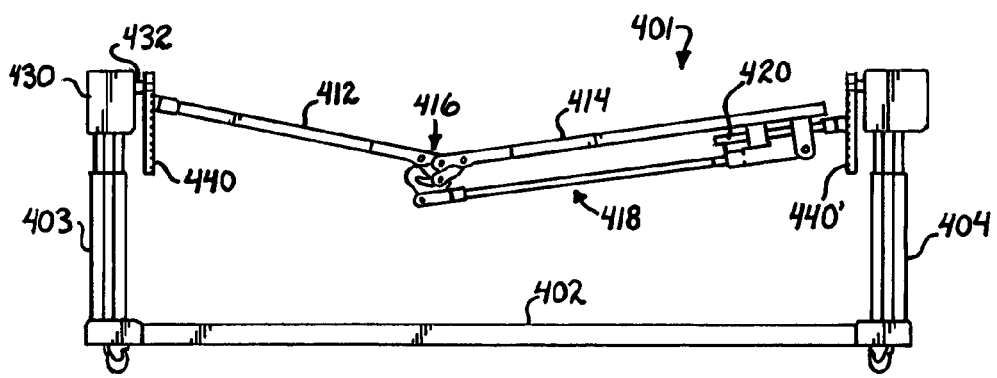
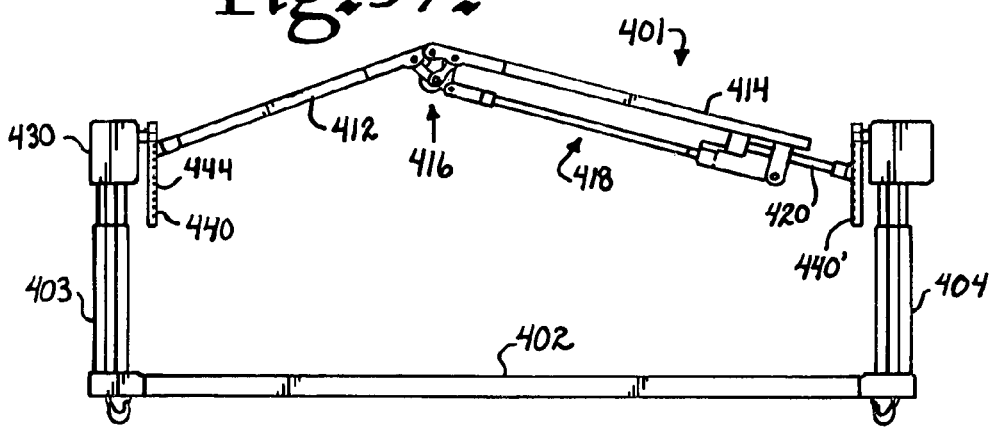

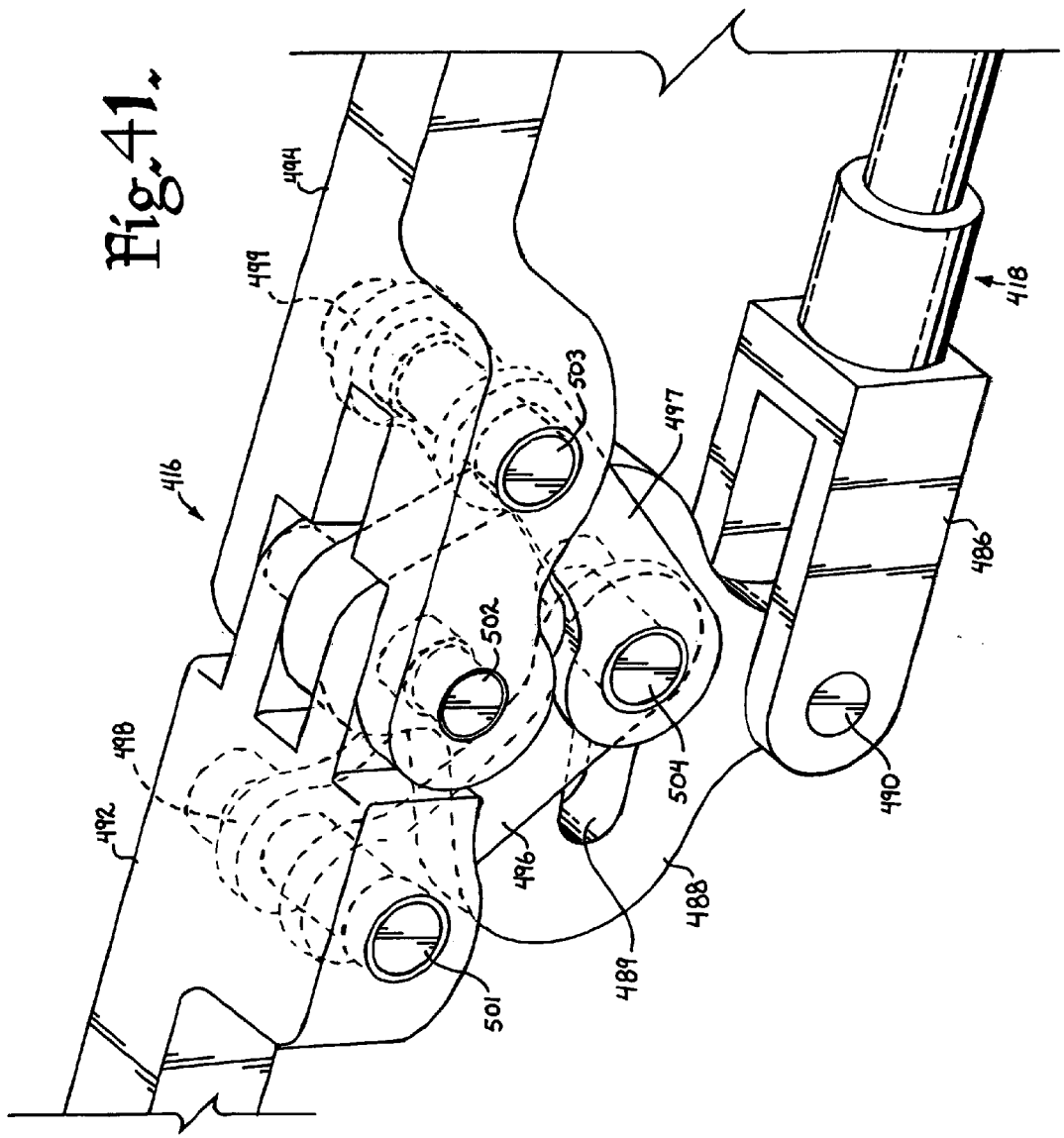

PATIENT POSITIONING SUPPORT STRUCTURE

CROSS-REFERENCE TO RELATED APPLICATIONS

This application is a continuation of U.S. Ser. No. 11/788,513, filed Apr. 20, 2007, now U.S. Pat. No. 7,565,708, which claimed the benefit of U.S. Provisional Application No. 60/798,288 filed May 5, 2006 and was also a continuation-in-part of U.S. patent application Ser. No. 11/159,494 filed Jun. 23, 2005, now U.S. Pat. No. 7,343,635, that is a continuation-in-part of U.S. patent application Ser. No. 11/062,775 filed Feb. 22, 2005, now U.S. Pat. No. 7,152,261, incorporated by reference herein.

BACKGROUND OF THE INVENTION

The present invention is directed to structure for use in maintaining a patient in a desired position during examination and treatment, including medical procedures such as imaging and surgery and in particular to such a structure that allows a surgeon to selectively position the patient for convenient access to the surgery site and providing for manipulation of the patient during surgery including the tilting, pivoting, angulating or bending of a trunk and/or a joint of a patient in a supine, prone or lateral position.

Current surgical practice incorporates imaging techniques and technologies throughout the course of patient examination, diagnosis and treatment. For example, minimally invasive surgical techniques, such as percutaneous insertion of spinal implants, involve small incisions that are guided by continuous or repeated intra-operative imaging. These images can be processed using computer software programs that produce three dimensional images for reference by the surgeon during the course of the procedure. If the patient support surface is not radiolucent or compatible with the imaging technologies, it may be necessary to interrupt the surgery periodically in order to remove the patient to a separate surface for imaging followed by transfer back to the operating support surface for resumption of the surgical procedure. Such patient transfers for imaging purposes may be avoided by employing radiolucent and other imaging compatible systems. The patient support system should also be constructed to permit unobstructed movement of the imaging equipment and other surgical equipment around, over and under the patient throughout the course of the surgical procedure without contamination of the sterile field.

It is also necessary that the patient support system be constructed to provide optimum access to the surgical field by the surgery team. Some procedures require positioning of portions of the patient's body in different ways at different times during the procedure. Some procedures, for example, spinal surgery, involve access through more than one surgical site or field. Since all of these fields may not be in the same plane or anatomical location, the patient support surfaces should be adjustable and capable of providing support in different planes for different parts of the patient's body as well as different positions or alignments for a given part of the body. Preferably, the support surface should be adjustable to provide support in separate planes and in different alignments for the head and upper trunk portion of the patient's body, the lower trunk and pelvic portion of the body as well as each of the limbs independently.

Certain types of surgery, such as orthopedic surgery, may require that the patient or a part of the patient be repositioned during the procedure while in some cases maintaining the sterile field. Where surgery is directed toward motion preservation procedures, such as by installation of artificial joints, spinal ligaments and total disc prostheses, for example, the surgeon must be able to manipulate certain joints while supporting selected portions of the patient's body during surgery in order to facilitate the procedure. It is also desirable to be able to test the range of motion of the surgically repaired or stabilized joint and to observe the gliding movement of the reconstructed articulating prosthetic surfaces or the tension and flexibility of artificial ligaments, spacers and other types of dynamic stabilizers before the wound is closed. Such manipulation can be used, for example, to verify the correct positioning and function of an implanted prosthetic disc, spinal dynamic longitudinal connecting member, interspinous spacer or joint replacement during a surgical procedure. Where manipulation discloses binding, sub-optimal position or even crushing of the adjacent vertebrae, for example, as may occur with osteoporosis, the prosthesis can be removed and the adjacent vertebrae fused while the patient remains anesthetized. Injury which might otherwise have resulted from a "trial" use of the implant post-operatively will be avoided, along with the need for a second round of anesthesia and surgery to remove the implant or prosthesis and perform the revision, fusion or corrective surgery.

There is also a need for a patient support surface that can be rotated, articulated and angulated so that the patient can be moved from a prone to a supine position or from a prone to a 90 position and whereby intra-operative extension and flexion of at least a portion of the spinal column can be achieved. The patient support surface must also be capable of easy, selective adjustment without necessitating removal of the patient or causing substantial interruption of the procedure.

For certain types of surgical procedures, for example spinal surgeries, it may be desirable to position the patient for sequential anterior and posterior procedures. The patient support surface should also be capable of rotation about an axis in order to provide correct positioning of the patient and optimum accessibility for the surgeon as well as imaging equipment during such sequential procedures.

Orthopedic procedures may also require the use of traction equipment such as cables, tongs, pulleys and weights. The patient support system must include structure for anchoring such equipment and it must provide adequate support to withstand unequal forces generated by traction against such equipment.

Articulated robotic arms are increasingly employed to perform surgical techniques. These units are generally designed to move short distances and to perform very precise work. Reliance on the patient support structure to perform any necessary gross movement of the patient can be beneficial, especially if the movements are synchronized or coordinated. Such units require a surgical support surface capable of smoothly performing the multi-directional movements which would otherwise be performed by trained medical personnel. There is thus a need in this application as well for integration between the robotics technology and the patient positioning technology.

While conventional operating tables generally include structure that permits tilting or rotation of a patient support surface about a longitudinal axis, previous surgical support devices have attempted to address the need for access by providing a cantilevered patient support surface on one end. Such designs typically employ either a massive base to counterbalance the extended support member or a large overhead frame structure to provide support from above. The enlarged base members associated with such cantilever designs are problematic in that they can and do obstruct the movement of C-arm and O-arm mobile fluoroscopic imaging devices and other equipment. Surgical tables with overhead frame structures are bulky and may require the use of dedicated operating rooms, since in some cases they cannot be moved easily out of the way. Neither of these designs is easily portable or storable.

Thus, there remains a need for a patient support system that provides easy access for personnel and equipment, that can be easily and quickly positioned and repositioned in multiple planes without the use of massive counterbalancing support structure, and that does not require use of a dedicated operating room.

SUMMARY OF THE INVENTION

The present invention is directed to a patient support system that permits adjustable positioning, repositioning and selectively lockable support of a patient's head and upper body, lower body and limbs in up to a plurality of individual planes while permitting tilting, rotation, angulation or bending and other manipulations as well as full and free access to the patient by medical personnel and equipment. The system of the invention may be cantilevered or non-cantilevered and includes at least one support end or column that is height adjustable. The illustrated embodiments include a pair of opposed independently height-adjustable end support columns. The columns may be independent or connected to a horizontally length-adjustable base. One support column according to the invention may be coupled with a wall mount or other stationary support. A patient support structure is connected to and bridges substantially between the pair of end supports. For example, in an embodiment according to the invention, the patient support structure is hingedly suspended between the end supports.

The patient support structure may be a frame or other patient support that is semi-constrained, having at least first and second hingeable or otherwise joined or connected portions, the first and second portions being selectively lockable in a first substantially planar orientation along a longitudinal axis of the support structure that resembles conventional constrained or fixed patient support structures. However, the hinged or semi-constrained support structure of the invention provides for the first and second portions that are also positionable and lockable in a plurality of angles with respect to one another, with each portion being movable to a position on either side of the first planar orientation. In other words, the patient support structure is capable of hinging or otherwise bending to form an angulation, break or joint, either upwardly or downwardly from a horizontal starting position and also when the support structure is in an inclined or declined position due to one of the support columns raising one end of the structure higher than another end. Furthermore, in addition to an "up" or "down" break, such a break or joint created by the two portions may be oriented from side-to-side, as when the support structure is rotated about a longitudinal axis thereof.

In a particular illustrated embodiment, articulation, jointing or breaking of the patient support structure at a central location between the pair of stationary end supports is supported by a cable drive system (tension band suspension). In another embodiment, a pull-rod assembly supports articulation to control the break or articulation angle and render the patient support structure rigid. Such an embodiment further includes a substantially fixed slider bar disposed at an end of the patient support, the patient support structure being supported by and slidingly movable along such slider bar with the bar following the angle of inclination of the patient support at such end. Other embodiments include cantilevered systems with connected or unconnected movable or telescoping base supports. The first and second patient support structure portions may be in the form of frames, such as rectangular frames or other support structure that may be equipped with support pads for holding the patient, or other structure, such as imaging tops which provide a flat surface.

The patient support structure and the support column or columns are coupled with respective rotation, articulation or angulation adjustment structure for positioning the first support portion with respect to a first column or end support and with respect to the second support portion and the second support portion with respect to the second column or end support. Rotation adjustment structure in cooperation with pivoting and height adjustment structure provide for the lockable positioning of the first and second patient support portions at a variety of selected positions and articulations with respect to the support columns including angulation coupled with Trendelenburg and reverse Trendelenburg configurations as well as providing for patient roll over in horizontal or tilted orientation. Lateral movement (toward and away from a surgeon) may also be provided by a bearing block feature. A pair of patient support structures (such as a support frame and an imaging table) may be mounted between end supports of the invention and then rotated in unison about a longitudinal axis to achieve 180° repositioning of a patient, from a prone to a supine position.

OBJECTS AND ADVANTAGES OF THE INVENTION

Therefore, it is an object of the present invention to overcome one or more of the problems with patient support systems described above. Further objects of the present invention include providing breaking or hinged patient support structures; providing such structures wherein such break or joint may be in any desired direction; providing such structures that include at least one base support structure that allows for vertical height adjustment; providing such a structure wherein such base support is located at an end of the patient support, allowing for patient positioning and clearance for access to the patient in a wide variety of orientations; providing such a structure that may be rotated about an axis as well as moved upwardly or downwardly at either end thereof; and providing apparatus and methods that are easy to use and especially adapted for the intended use thereof and wherein the apparatus are comparatively inexpensive to make and suitable for use.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 2 is an enlarged and partial side elevational view of a portion of the support structure of FIG. 1.

FIG. 3 is an enlarged and partial top plan view of the support structure of FIG. 1.

FIG. 4 is an enlarged and partial perspective view of a portion of the structure of FIG. 1.

FIG. 7 is an enlarged and partial perspective view of a first hinge of the structure of FIG. 1.

FIG. 8 is an enlarged and partial perspective view of a cooperating second hinge of the structure of FIG. 1.

FIG. 12 is an enlarged and partial perspective view of a portion of the structure of FIG. 1 showing a cable drive motor and winch cylinders.

FIG. 13 is a partial perspective view of a patient support frame of the structure of FIG. 1.

FIG. 14 is a partial perspective view of a patient imaging top for replacement with the patent support frame of FIG. 13.

FIG. 15 is a reduced perspective view of the structure of FIG. 1 shown with an imaging top of FIG. 14 replacing the support frame of FIG. 13 and shown in a planar inclined position.

FIG. 16 is a perspective view of the structure of FIG. 15 shown in a planar tilted position.

FIG. 17 is a perspective view of the structure of FIG. 15 shown in a planar inclined and tilted position.

FIG. 24 is an enlarged side elevational view of the structure of FIG. 1 shown in an upward breaking, inclined and tilted position.

FIG. 25 is a is a perspective view of a second embodiment of a patient support structure according to the invention including a patient support frame and an imaging table shown in a first spaced orientation.

FIG. 26 is a perspective view of the patient support structure of FIG. 25 shown tilted in an intermediate position during a rotation as would be used for a patient rollover.

FIG. 27 is a perspective view of the structure of FIG. 25 shown further tilted in a second intermediate position during rotation.

FIG. 28 is a perspective view of the structure of FIG. 25 shown after rotation to a final flipped position.

FIG. 29 is a perspective view similar to FIG. 25 showing the patient support frame and the imaging table in a second spaced orientation.

FIG. 30 is a front elevational view of a third embodiment of a patient support structure according to the invention.

FIG. 31 is a front elevational view of a fourth embodiment of a patient support structure according to the invention.

FIG. 32 is a perspective view of a fifth embodiment of a patient support structure according to the invention shown in a planar inclined position.

FIG. 33 is a perspective view of the structure of FIG. 32 shown in an inclined and upward breaking position.

FIG. 35 is a reduced side elevational view of a sixth embodiment of a patient support structure according to the invention shown in a substantially horizontal and planar position.

FIG. 36 is a reduced side elevational view of the structure of FIG. 35 shown in a symmetrical downward breaking position.

FIG. 37 is a reduced side elevational view of the structure of FIG. 35 shown in a symmetrical downward breaking position.

FIG. 41 is an enlarged and partial perspective view of the structure shown in FIG. 40.

DETAILED DESCRIPTION OF THE ILLUSTRATED EMBODIMENTS

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
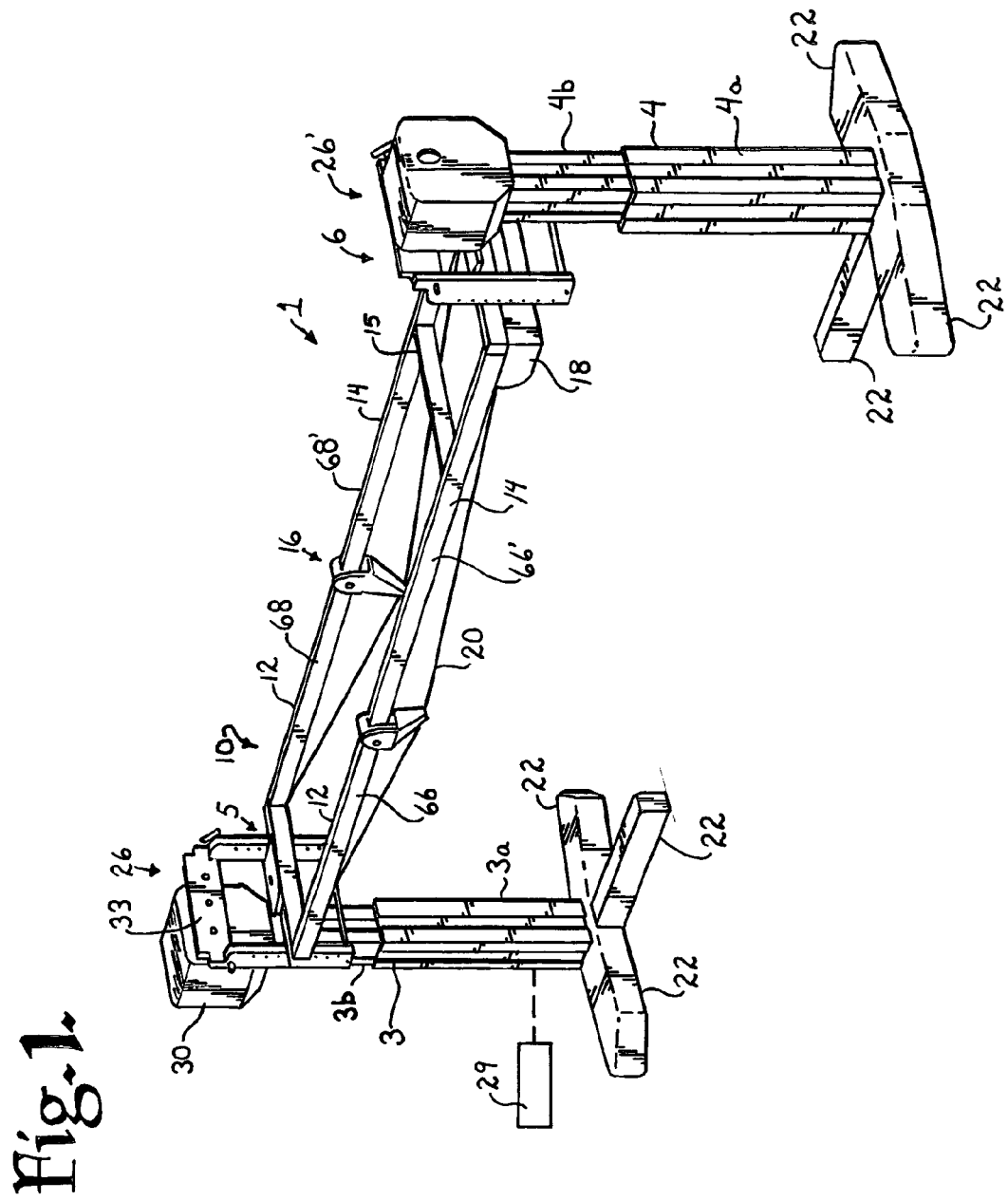
FIG. 1 is a perspective view of a patient support structure according to the invention.

Referring now to the drawings, a patient positioning support structure according to the invention is generally designated by the reference numeral 1 and is depicted in FIGS. 1-12. The structure 1 includes first and second upright support piers or columns 3 and 4 which are illustrated as independent, stationary floor base support structures as shown in FIG. 1 or may be connected to one another by a non-telescoping base support as illustrated in the embodiment shown in FIGS. 25-28. In some embodiments according to the invention as shown, for example, in FIGS. 32-34, the base connection places the columns in a selectively telescoping relationship. It is also foreseen that in certain embodiments according to the invention, one of the support columns may be replaced by a conventional operating room table, or may even be a wall mount. In the first illustrated embodiment, the upright support column 3 is connected to a first support assembly, generally 5, and the upright support column 4 is connected to a second support assembly, generally 6. Between them, the support assemblies 5 and 6 uphold a removable elongate, articulate jointed or breaking patient holding or support structure, generally 10 and optionally, a second removable patient support structure that will be described with respect to another embodiment of the invention. The illustrated support structure 10 includes a first frame section 12, a second frame section 14 with a transverse support cross bar 15, and a pivot or hinge assembly, generally 16. In the illustrated embodiment, the pivot assembly further includes a cable drive system including a dual winch 18 and cooperating cables 20.

The columns 3 and 4 are supported by outwardly extending feet 22 that may or may not include spaced apart casters or wheels (not shown) each equipped with a floor-lock foot lever for lowering the feet 12 into a floor-engaging position as shown in FIG. 1. The columns 3 and 4 each include two or more telescoping lift arm segments 3a, 3b and 4a, 4b, respectively that permit the height of each of the columns 3 and 4 to be selectively increased and decreased in order to raise and lower all or a selected portion of the connected patient support structure 10. It is foreseen that the vertical supports 3 and 4 may be constructed so that the column 3 has a greater mass than the support column 4 or vice versa in order to accommodate an uneven weight distribution of the human body. Such reduction in size at the foot end of the system 1 may be employed in some embodiments to facilitate the approach of personnel and equipment.

Each of the support assemblies 5 and 6 generally includes a rotation subassembly 26 and 26' and an angulation subassembly 27 and 27', respectively, that are interconnected as will be described in greater detail below and include associated power source and circuitry linked to a controller 29 (FIG. 1) for cooperative and integrated actuation and operation. The rotational subassemblies 26 and 26' enable coordinated rotation of the patient support structure 10 about a longitudinal axis of the structure 1. The angulation subassemblies 27 and 27' shown in FIGS. 2 and 3 enable the selective hinging, articulation or breaking of the support 10 at the hinge assembly 16 at desired levels and increments as well as selective tilting of the frame portions 12, 14 with respect to a longitudinal axis of such frame portion.

Figure 5:
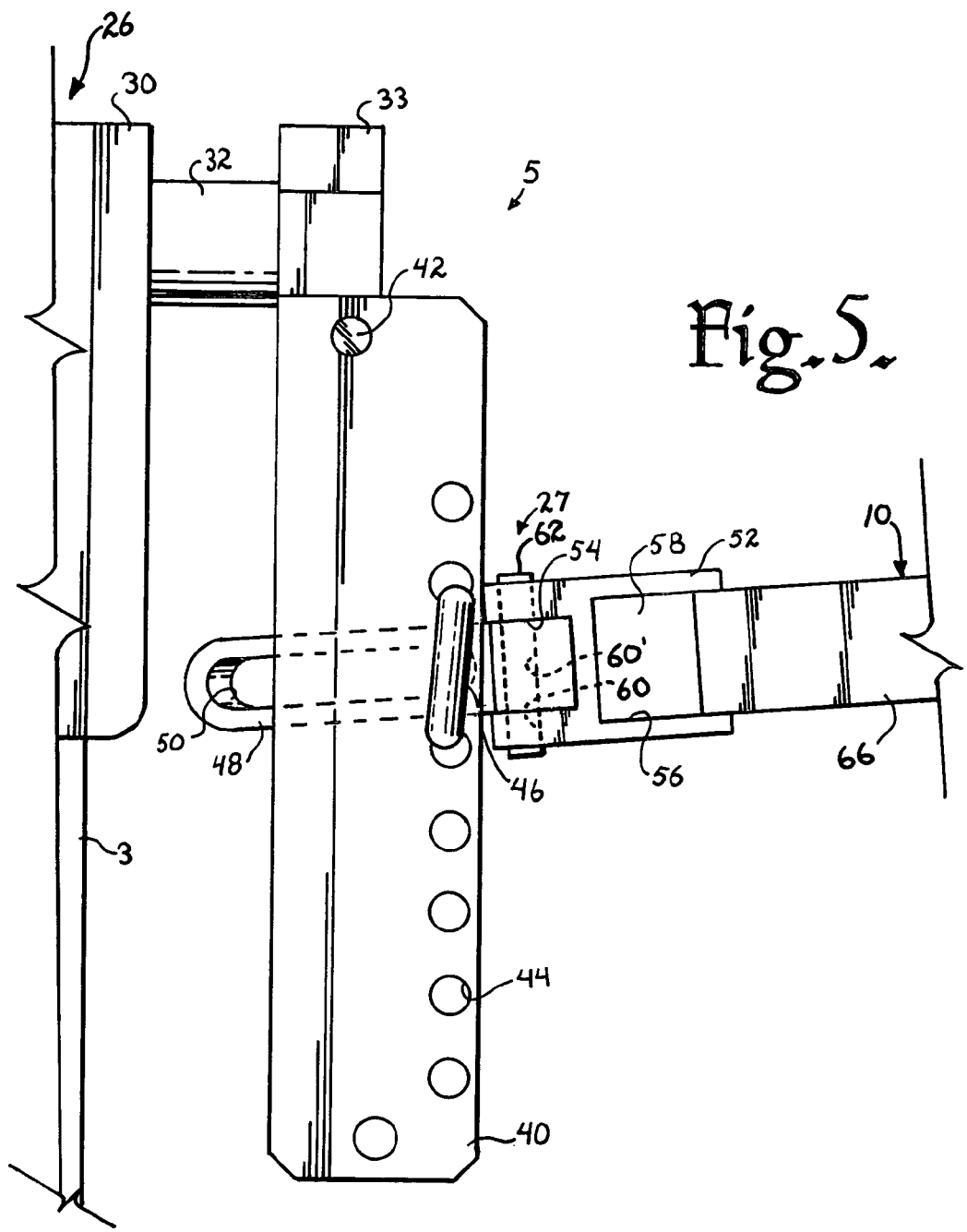
FIG. 5 is an enlarged and partial side elevational view of a portion of the structure of FIG. 1.

The rotation subassembly or mechanism 26, shown in FIGS. 1 and 5, includes at least one motor housing 30 surmounting the support column 3. In the illustrated embodiment, only one rotational motor is provided, but it is foreseen that a cooperating motor may also be mounted on the support column 4. A main rotational shaft 32 extends from the motor housing 30 that turns a rotation structure 33. The rotation structure 33 in turn rotates the connected patient support 10 about a longitudinal axis as will be described in greater detail below. The motor housing 30 contains a rotary electric motor or other actuator drivingly engaged with the shaft 32. The rotation mechanism 26 is operated by actuating the motor using a switch or other similar means. The rotation structure 33 is fixed to the shaft 32 at a location spaced from the motor housing 30 and the support column 3 to provide clearance for rotation of the connected patient support structure 10.

As shown in FIGS. 4 and 5, the rotation structure 33 is attached to a pair of translation posts or H-bar posts 40 disposed at either end of the rotation structure 33. The posts 40 are each attached to the structure 33 by a pin 42, bolt, or other fixing structure. A plurality of cooperating apertures 44 formed in the posts 40 provide passageway for a pivot pin 46 to extend therethrough. The pivot pin 46 is receivable in each cooperating pair of apertures 44 allowing for selective placement of a translation connector 48 that is sized and shaped to be received between the pair of posts 40 and also receive the pivot pin 46 therethrough. The pin 46 and connector 48 are thus positionable in an orientation transverse to the longitudinal extension of the support 10 at a variety of heights to be selected by the surgeon and readily changeable, even during surgery if necessary, to vary the height of the frame section 12. The multiple location or height feature is also advantageous when more than one frame or patent structure is mounted in tandem as shown, for example in FIGS. 25-29. The position of the frame or other structure may be desirably changed to provide close proximity to an imaging top with a distance between a patient support and an imaging top being expandable or reduceable depending upon the size or other attributes of a patient and surgical or other requirements. As illustrated in FIG. 5, the connector 48 has a slot 50 for receiving the pivot pin 46.

Also with reference to FIGS. 4 and 5, the translation connector 48 is in turn attached to a pivot connector 52. The pivot connector 52 includes first and second outwardly opening and opposed slots 54 and 56. The first slot 54 is sized and shaped for receiving the translation connector 48 and the second slot is sized and shaped for receiving an end connection 58 of the frame section 12. The pivot connector 52 further includes a through aperture or bore 60 running substantially perpendicular to the slot 54 and communicating therewith. The aperture 60 is sized and shaped to receive a pivot pin 62 therethrough. The connector 48 also includes a through bore 60' that receives the pivot pin 62. The swivelable connection provided by the pin 62 allows for some forward and rearward lateral movement of the attached frame end connection 58 and thus the frame section 12, providing a degree of freedom and clearance needed for rotation the patient support about a longitudinal axis of a patient. The slot 56 is sized and shaped to frictionally engage the frame end connection 58, thus securely fixing the end connection 58 to the pivot connector 52. The frame end connection 58 is in turn fixed to each of elongate frame members 66 and 68 of the frame section 12. The frame members 66 and 68 are each hingedly connected to the hinge assembly 16 to be described in greater detail below. Pivoting of the translation connector 48 with respect to the pin 46 provides for selected articulation of the frame section 12 (that includes the end connection 58 and the frame members 66 and 68) and/or the entire support 10 with respect to the support pier or column 3.

Figure 6:
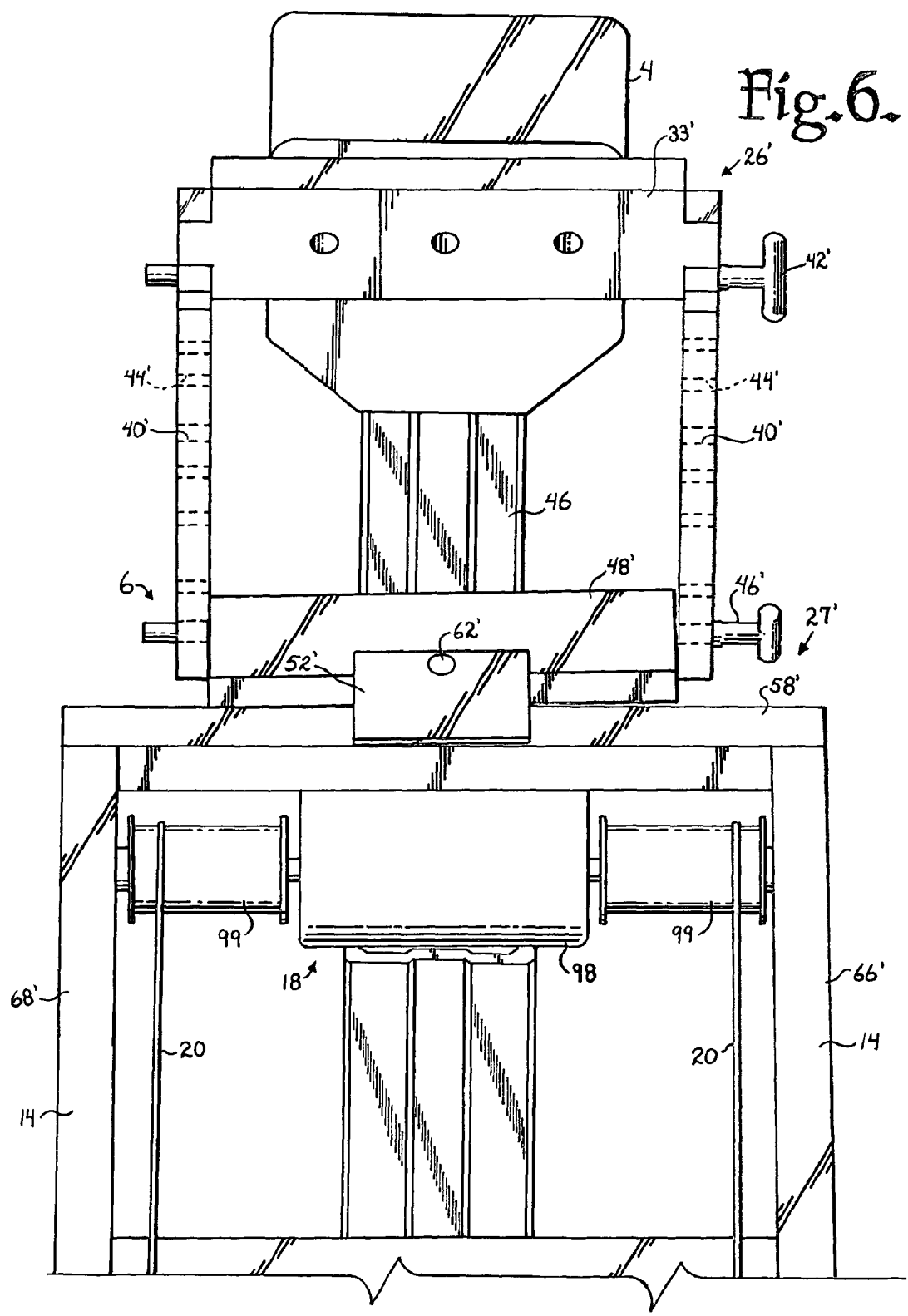
FIG. 6 is an enlarged and partial perspective view of a portion of the structure of FIG. 1.
Figure 9:
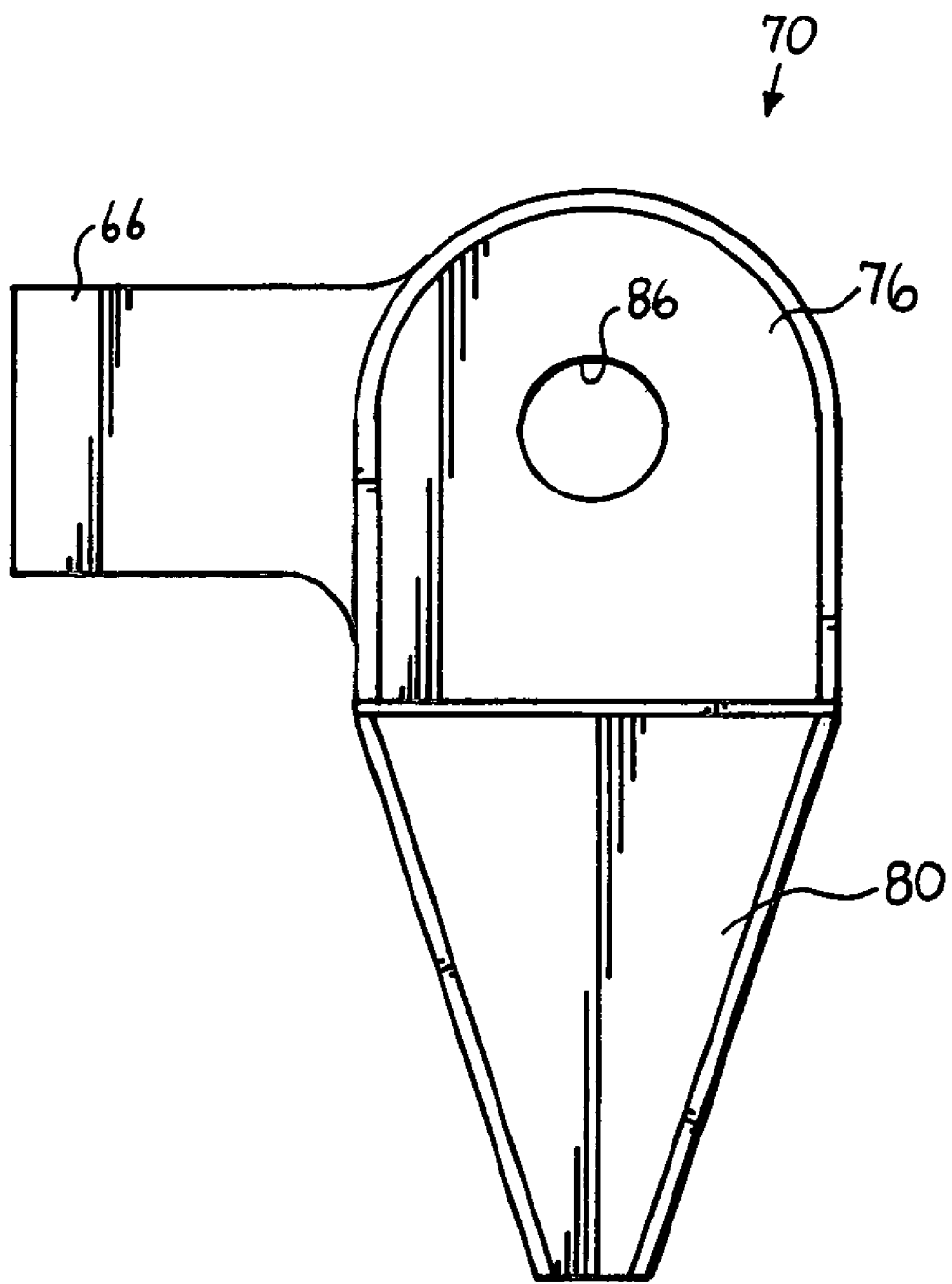
FIG. 9 is an enlarged and partial elevational view of the hinge of FIG. 7.
Figure 10:
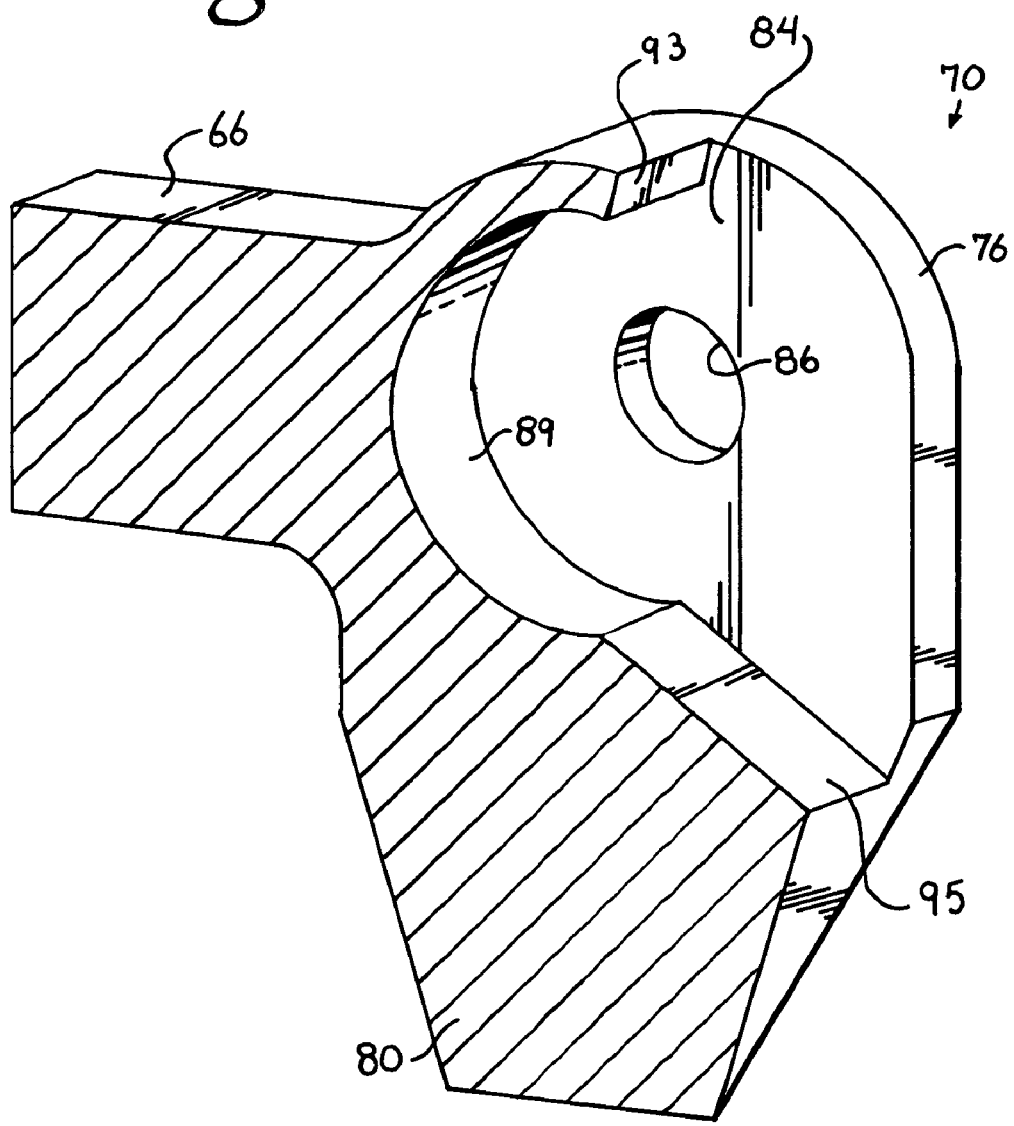
FIG. 10 is an enlarged and partial perspective view of an outer portion of the hinge of FIG. 7 with portions broken away to show the detail thereof.
Figure 11:
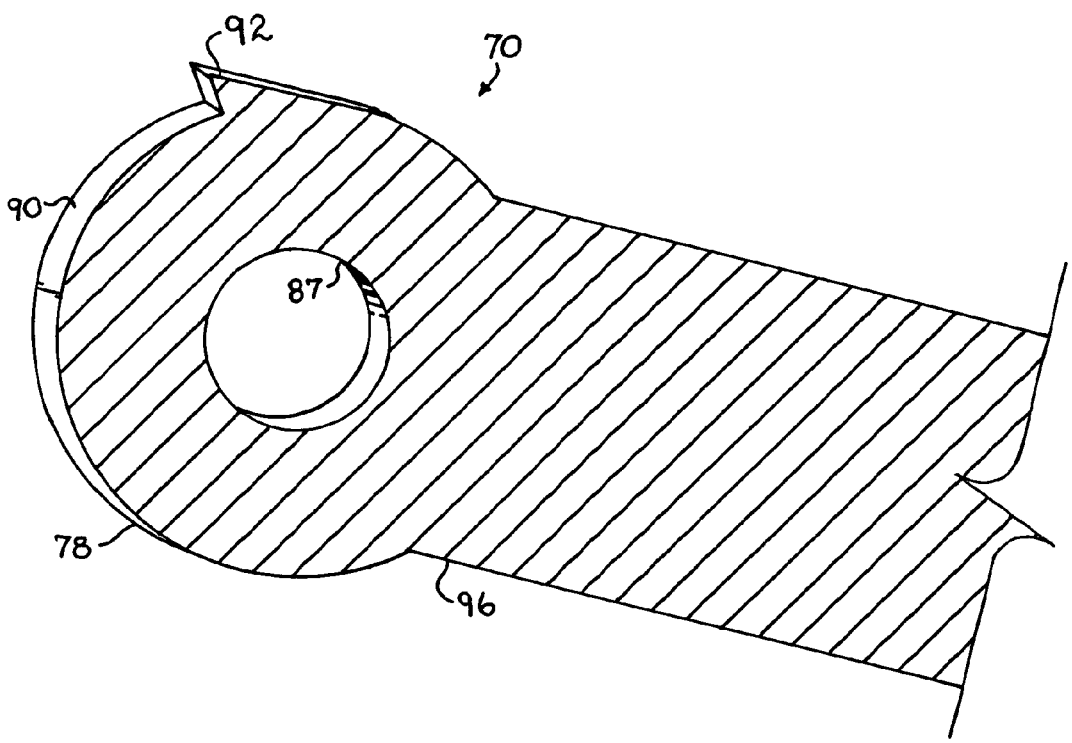
FIG. 11 is an enlarged and partial perspective view of an inner portion of the hinge of FIG. 7 with portions broken away to show the detail thereof.

With reference to FIG. 6, at the support pier or column 4, the support assembly 6 is substantially similar to the support assembly 5 with the exception that the rotation subassembly 26' can be passive and, therefore, not include a motor. However, the support pier or column 4 preferably includes a powered mechanism to provide selective height adjustment of the subassembly 26'. A rotation structure 33' is spaced from and freely rotatable with respect to the column 4. The structure 33' includes a shaft (not shown) extending outwardly therefrom similar to the rotation shaft 32, the shaft being rotatingly received in an aperture in the support column 4.

The rotation subassembly 26' and the angulation subassembly 27' otherwise include elements identical to or substantially similar to the elements of the subassemblies 26 and 27. Specifically, H-bar posts 40', pin 42', apertures 44', pivot pin 46', translation connector 48', slot 50', pivot connector 52', end connector 58' and pivot pin 62', are identical or substantially similar in form and cooperate with other elements identically or substantially similarly to what has been described previously herein with respective H-bar posts 40, pin 42, apertures 44, pivot pin 46, translation connector 48, slot 50, pivot connector 52, end connector 58 and pivot pin 62.

The frame 14 further includes frame members 66' and 68' that are each fixed to the end connector 58'. The frame members 66' and 68' are pivotally or hingedly connected to respective frame members 66 and 68 by the hinge assembly 16. Specifically, the frame member 66 is attached to the frame member 66' by the hinge mechanism 70 and the frame member 68 is attached to the frame member 68' by the hinge mechanism 72.

Figure 21:
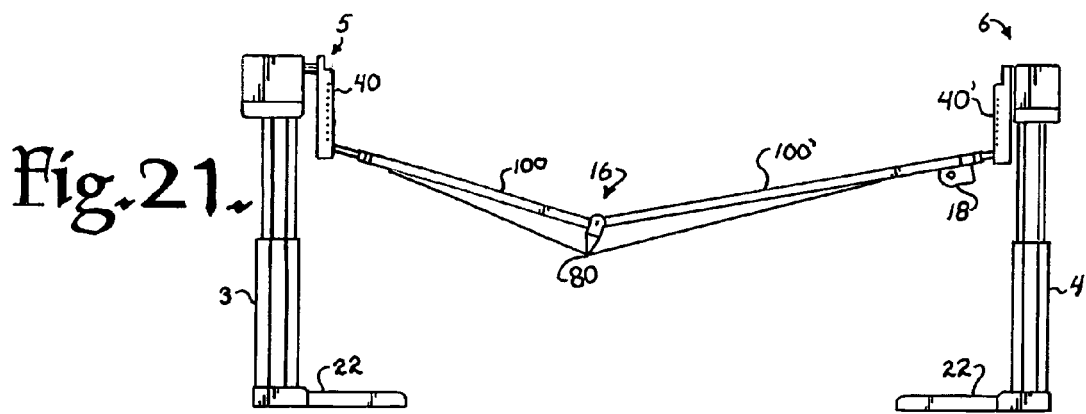
FIG. 21 is a side elevational view of the structure of FIG. 15 shown in a symmetrical downward breaking position.

With particular reference to FIGS. 3, 7 and 9-11, the hinge mechanism 70 includes an outer member 76 and an inner member 78. The outer member 76 is fixed or may be integral with the elongate frame member 66, while the inner member 78 is integral or otherwise fixed to the frame member 66'. The outer member 76 further includes an extension 80 with a groove 82 for receiving and guiding the cable 20. The extension 80 tapers in a direction from the outer member interior 84 to the groove 82. The extension 80 is configured to cause a slight upward break or bend of the support 10 when the extension 80 comes into contact with the cable 20 at the groove 82. In that way, when the cables 20 are reeled in to shorten the hypotenuse of the triangle formed by the cable, the section 12 and the section 14, the sections 12 and 14 move toward one another, resulting in the upward break as illustrated, for example, in FIG. 18. The downward break or joint illustrated, for example, in FIG. 21 is a result of lengthening the cable 20 distance and allowing gravity to drop the hinge 70. The extension 80 is shaped to extend slightly inwardly toward a longitudinal axis A of the support 10, thereby guiding the cable 20 along a path within a periphery of the frame sections 12 and 14 when the extension 80 is in contact with the cable 20 when in a downward breaking configuration directed toward the cable with the cable 20 being received at the groove 82.

It is foreseen that if an exclusively upward breaking or jointing embodiment is desired according to the invention, the sections 12 and 14 may be positioned with respect to two end columns to always include a slight upward break, joint or bend at the hinge or pivot between the sections 12 and 14. When the telescoping base is actuated to move the columns toward one another, the sections 12 and 14 would automatically further break or articulate upwardly and toward one another. Downward breaking or jointing would not be possible in such an embodiment as the maximum distance between the two end columns would still ensure a slight upward break or hinge between the sections 12 and 14. Such an embodiment would be acceptable for use because patient holding pads could be positioned on the frames 12 and 14 such that the patient would be in a substantially horizontal position even when there is a slight upward bend or break at the hinge between the sections 12 and 14.

Returning to the hinge 70 of illustrated embodiment, the inner member 78 is slidingly and rotatably receivable in an interior 84 of the outer member 76. The outer member has a pair of pivot apertures 86 and the inner member has a pivot aperture 87, the apertures cooperating to create a through bore for receiving a pivot pin 88 through both the inner and outer hinge members. The interior 84 includes a curved partially cylindrical surface 89 for slidingly receiving a cooperating outer rounded and partially cylindrical surface 90 of the inner member 78. The inner member 78 further includes a downward breaking stop or projection 92 that limits a downward pivot (in a direction toward the cables 20) of the hinge 70 in the event the cables 20 should fail. The stop 92 abuts against a surface 93 of the interior 84. In the illustrated embodiment, the stop 92 limits the extent of rotation or hinging of the section 66 with respect to the section 66' to about twenty-five degrees. Upward pivot (in a direction away from the cables 20) is limited by abutment of an inner planar surface 95 with a planar surface 96 of the hinge inner member 78.

With particular reference to FIG. 8, the hinge mechanism 72 is substantially a mirror image of the hinge mechanism 70 and therefore includes the following elements: a hinge outer member 76', an inner member 78', an extension 80' with a groove 82', an interior 84', pivot apertures 86', a pivot pin 88', a curved surface 89'(not shown), an outer surface 90' (not shown), a stop 92' (not shown), an abutment surface 93', an inner planar surface 95' and a planar surface 96' that are identical or substantially similar in shape and function to the respective hinge outer member 76, inner member 78, extension 80, groove 82, interior 84, pivot apertures 86, pivot pin 88, curved surface 89, outer surface 90, stop 92, abutment surface 93, inner planar surface 95 and planar surface 96 described herein with respect to the hinge 70.

It is noted that other hinge or pivot mechanisms may be utilized in lieu of the hinge assembly 16. For example, the polyaxial joint 95 illustrated and described in Applicant's U.S. Pat. Ser. No. 7,152,261 and pending U.S. patent application Ser. No. 11/159,494 filed Jun. 23, 2005, may be incorporated into the patient support structure 10 at the break or joint between the sections 12 and 14. The disclosures of U.S. Pat Ser. No. 7,152,261 and U.S. patent application Ser. No. 11/159,494 are incorporated by reference herein. It is foreseen that a rotating universal joint operated type of hinge mechanism could be used with the invention, etc.

With particular reference to FIGS. 6 and 12, the cable drive system 18 includes a rotary motor 98 cooperating with and driving by rotation a pair of winch cylinders 99 disposed on either side of the motor 98. The motor 98 and cylinders 99 are mounted to the end connector 58' located near the support column 4. Each cable 20 is attached to one of the winch cylinders 99 at one end thereof and to the end connector 58 at the other end thereof. In a first longitudinal position wherein the section 12 is substantially planar with the section 14, the cables 20 are wound about the winch cylinders 99 an amount to provide enough tension in the cables 20 to maintain such a substantially planar orientation and configuration, with the hinge extensions 82 and 82' being in contact with each of the cables 20. The motor 98 is preferably low speed and high torque for safely winding both of the cables 20 simultaneously about the cylinders 99 to draw the section 12 toward the section 14 to result in an upward breaking or jointing configuration with the hinges 70 and 72 disposed in spaced relation with the cables 20 and the hinges 70 and 72. The motor 98 may be reversed, reversing the direction of rotation of the winch cylinders 99 for slowly unwinding the cables 20 to a downward breaking or jointing configuration. As the cables 20 unwind, gravity draws the support sections 12 and 14 downward with the cables 20 being received in the grooves 82 and 82' of the hinge extensions 80 and 80'. As the cables 20 slacken, the hinges 70 and 72 continue to lower pressing down upon the cables 20.

It is noted that the frame sections 12 and 14 are typically equipped with pads (not shown) or other patient holding structure, as illustrated, for example, in Applicant's U.S. Pat. Ser. No. 5,131,106, the disclosure of which is incorporated by reference herein. It is foreseen that such patient holding structure could translate or glide along the frame sections 12 and 14. Furthermore, with respect to FIGS. 13 and 14, the frame member sections 66 and 68 of section 12 and the frame member sections 66' and 68' of the section 14 may be replaced with substantially rectangular imaging tops or sections 100 and 101' respectively. Each of the sections 100 and 101' having elongate slots 101 formed therein to allow for attachment of the hinge mechanisms 70 and 72 in a manner identical or substantially similar to what has been described herein with respect to the frame sections 12 and 14.

With reference to FIGS. 15-17, the imaging sections 100 and 100' are illustrated, replacing the frame sections 12 and 14 of the embodiment disclosed in FIGS. 1-12. Each of FIGS. 15-17 represent configurations in which the cable drive 18 is tensioned such that the sections 100 and 100' are kept in a substantially coplanar configuration. FIG. 15 illustrates a configuration in which the column 3 is telescoped upwardly with the frame sections hinging at the support assemblies 5 and 6, resulting in an inclined position or configuration of the entire patient support. In the illustrated embodiment, the section 100 would preferably receive a patient's head. Therefore, FIG. 15 illustrates a reverse Trendelenburg position or orientation. FIG. 16 illustrates the sections 100 and 100' again in a substantially common plane with both sections being rotated to a tilted position produced by a powered rotation of the sub assemblies 26 and passive rotation of the assembly 26' with both columns 3 and 4 otherwise holding the sections 100 and 100' at the same height. FIG. 17 illustrates both tilting due to rotation of the assemblies 26 and 26' and also a sloping or inclined position with the column 4 being extended vertically. Thus, FIG. 17 illustrates a Trendelenburg position or orientation with both the sections 100 and 100' remaining in substantially the same plane. It is foreseen that a bearing block assembly at one or both ends of the table provides for some lateral translation to prevent binding of the hinge mechanisms.

Figure 18:
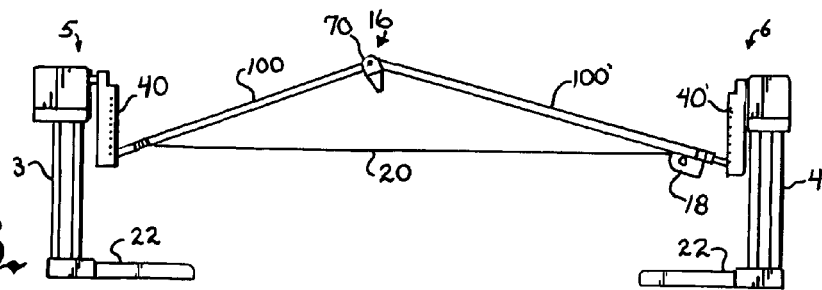
FIG. 18 is a side elevational view of the structure of FIG. 15 shown in a symmetrical upward breaking position.
Figure 19:
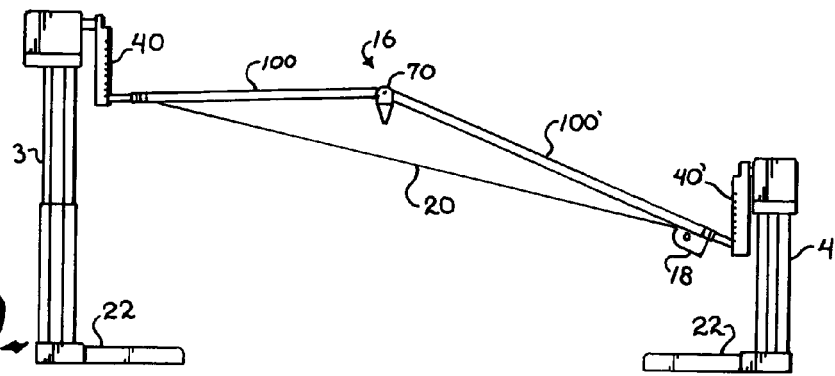
FIG. 19 is a side elevational view of the structure of FIG. 15 shown in a first inclined and upward breaking position.
Figure 20:
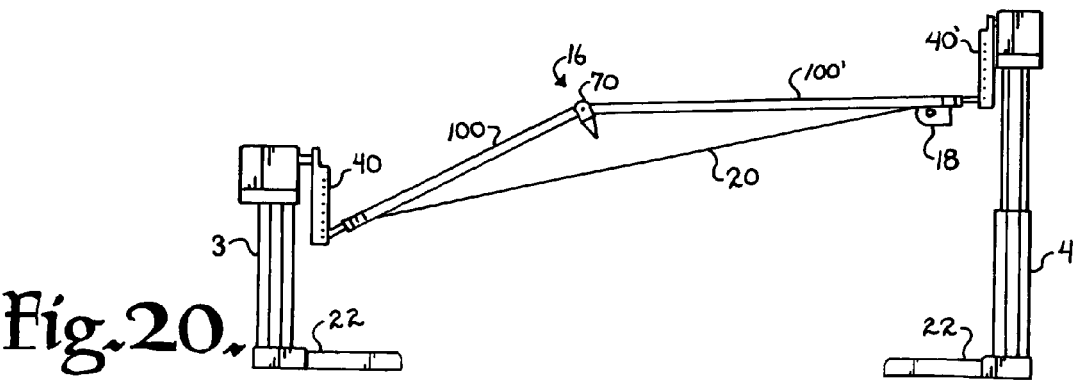
FIG. 20 is a side elevational view of the structure of FIG. 15 shown in a second inclined and upward breaking position.

With reference to FIGS. 18-20, there is illustrated three upward breaking or hinging configurations of the structure 1. FIG. 18 illustrates a symmetrical upward breaking configuration wherein the columns 3 and 4 are holding the respective support assemblies 5 and 6 at substantially the same height with the cables 20 being shortened by rotation of the winch motor to result in an upward break or joint in the hinge assembly 16. FIG. 19 illustrates the column 3 being extended to a maximum height and the cables reeled to shorten a distance between the sections 100 and 100'. An example of such an upward break or joint with reverse Trendelenburg would be a head or column 3 height of 43 inches, a foot or column 4 height of 24 inches and a 35 degree upward break with zero degree roll. FIG. 20 illustrates an upward breaking Trendelenburg with the column 4 being extended to a maximum height.

Figure 22:
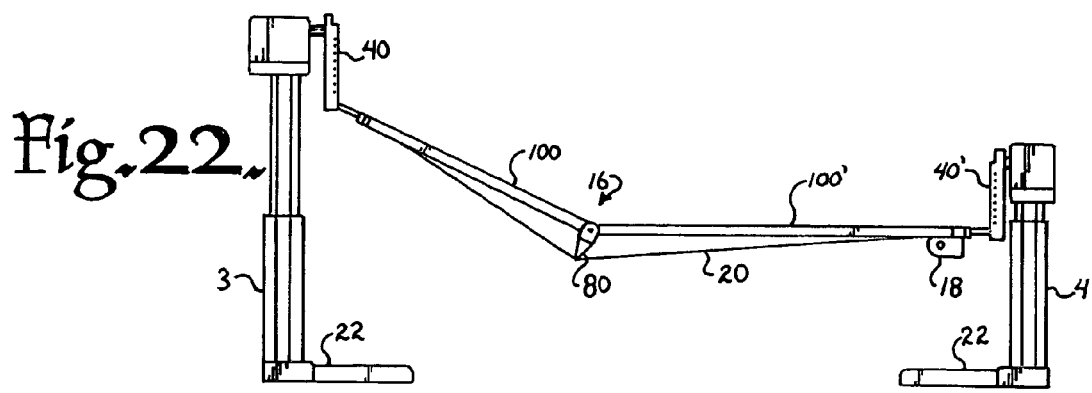
FIG. 22 is a side elevational view of the structure of FIG. 15 shown in a first inclined and downward breaking position.
Figure 23:
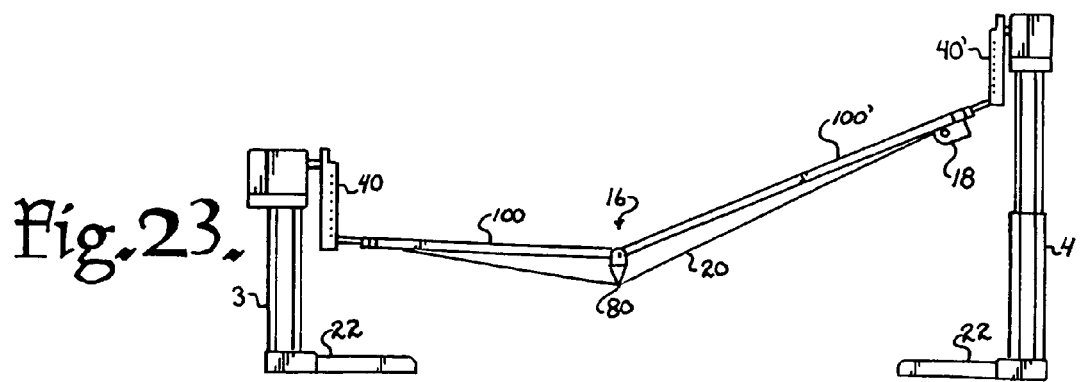
FIG. 23 is a side elevational view of the structure of FIG. 15 shown in a second inclined and downward breaking position.

With reference to FIGS. 21-23, there is illustrated three downward breaking configurations of the structure 1. FIG. 21 illustrates a symmetrical downward breaking configuration wherein the columns 3 and 4 are holding the support assemblies 5 and 6 respectively, at the same height with the cables 20 being unwound or slackened to result in a downward break or joint in the hinge assembly 16, the hinges 70 and 72 contacting the cables 20. FIG. 22 illustrates a downward breaking reverse Trendelenburg with the column 3 being extended to a maximum height resulting in a patent's head end being at a maximum height. FIG. 23 illustrates a downward breaking Trendelenburg with the column 4 being extended to a maximum height.

It is noted that in each of the configurations illustrated in FIGS. 18-23, the sub-assemblies 26 may be rotated in either direction, resulting in a tilted or rotated as well as upwardly or downwardly broken or hinged configuration. For example, FIG. 24 illustrates the structure 1 with support frame sections 12 and 14 positioned in a configuration similar to that illustrated in FIG. 19, but also including rotation, resulting in a tilting and upwardly breaking or jointed configuration of the structure 1. An example of the position illustrated in FIG. 24 would be: a head or column 3 height of 41 inches, a foot or column 4 height of 34 inches and a 35 degree upward break or joint with 10 degree roll.

With reference to FIGS. 25-29, another structure, generally 102 according to the invention is illustrated. The structure 102 utilizes all of the elements described herein with respect to the structure 1 and therefore the same references numerals are used for the same elements or features. The structure 102 differs from the structure 1 in that the H-bar posts 40 and 40' are replaced or modified to be extended H-bar posts 40A and 40A', allowing for the mounting of two elongate structure 10 and cooperating cable drives 18. In the embodiment shown in FIG. 25, one of the structures 10 includes the frame member 12 and 14 while the other structure is an imaging top having sections 100 and 100'. As previously described herein, the cooperating H-bar posts 40A and 40A' equipped with a plurality of apertures allows for the placement of the support structures 10 at a variety of locations. For example, FIGS. 25-28 illustrate a first spaced orientation of the elongate frame with respect to the elongate imaging top with the imaging top located at a "lower" position identified by the reference letter L. The identical components are shown in FIG. 29 with the imaging top located at a "mid-position" identified by the reference letter M, illustrating a more compact or closely spaced orientation of the elongate frame with respect to the elongate imaging top than what is shown in FIG. 25.

As illustrated in FIGS. 25-28, the structure 102 provides for the complete rotation and thus a roll-over of a patient by actuation of the motor of the rotation subassembly 26 using the controller 29. The structure 102 shown in FIGS. 25-29 is further illustrated with a non-telescoping base support 110 fixed to each of the columns 3 and 4 and rollers or castors 112 at the base of the structure 102.

With reference to FIGS. 30 and 31, another embodiment or system according to the invention, generally 200 is illustrated. The system 200 broadly includes an elongate length-adjustable base 202 surmounted at either end by respective first and second upright support piers or columns 203 and 204 which are connected to respective first and second support assemblies, generally 205 and 206. Between them, the support assemblies 205 and 206 uphold an elongated breaking, hingeable or pivotable patient support structure, generally 210. The hinge structure is described in detail in Applicants's U.S. Pat. Ser. No. 7,152,261 and also U.S. patent application Ser. No. 11/159,494, both disclosures of which are incorporated by reference herein. The embodiment 200A illustrated in FIG. 31 differs from the structure 200 only in that the length-adjustable base 202 is replaced by a first base 220 attached to the pier 203 and a second base 222 attached to the pier 204. All of the bases 202, 220 and 222 include castors or rollers 230 or some other movable structure to allow the piers 203 and 204 to move toward and away from one another during upward or downward breaking of the structure 210.

It is foreseen that cable drives as described herein, other types of motor drives including screw drives, universal joints, hydraulic systems, and the like, may be utilized to facilitate both upward and downward breaking of the support structure 210.

Figure 34:
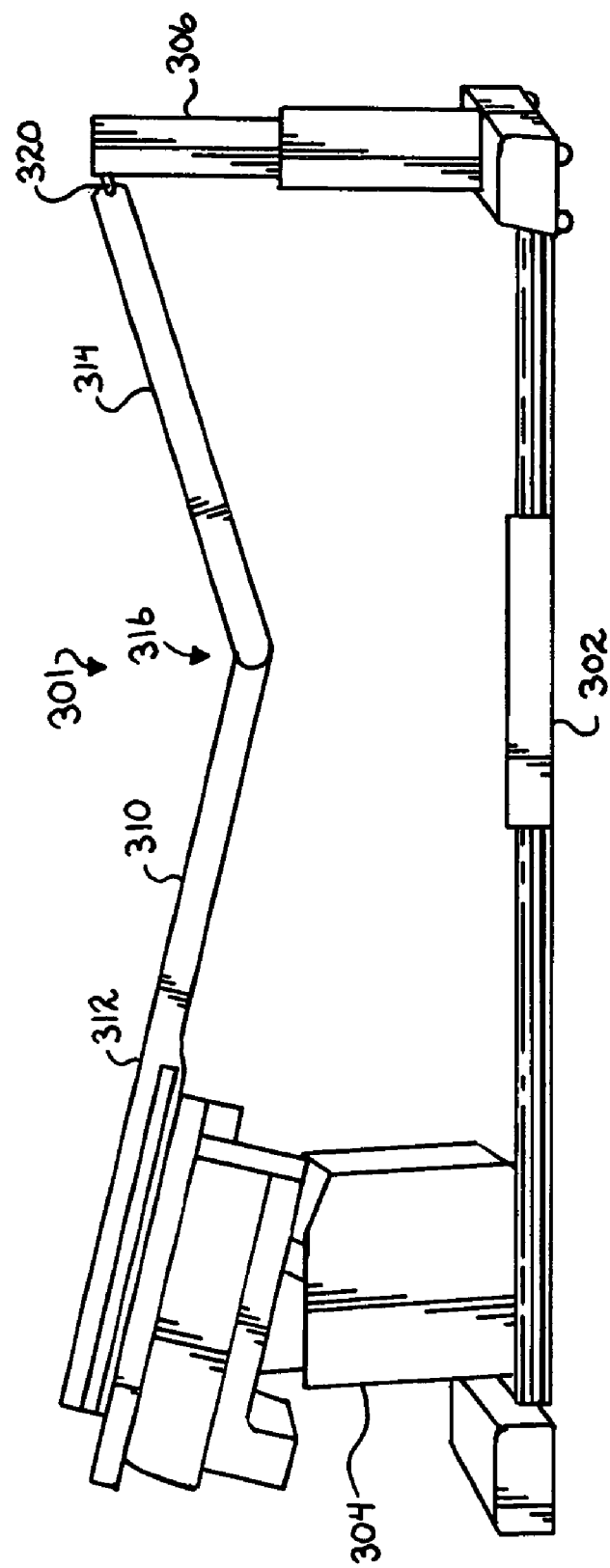
FIG. 34 is a perspective view of the structure of FIG. 32 shown in a substantially symmetrical downward breaking position.

Another patient support structure according to the invention, generally 301, is illustrated in FIGS. 32-34. The structure 301 generally includes a horizontally telescoping floor mounted base 302, a conventional or standard telescoping and inclinable operating table support structure 304, a telescoping end support or pier 306 and a hinged or pivotally upwardly and downwardly breaking or jointing support structure 310 connected to both the structure 304 and the pier 306. The patient support structure 310 further includes a first cantilevered section 312 and a second section 314. The first section 312 is fixed to and extends from the operating table support 304. The second section is attached to the pier 306 by a hinge or pivoting assembly 320, such as the support assembly 5 described herein with respect to the structure 1. The hinge mechanism 316 disposed between the support sections 312 and 314 may be a conventional hinge, pivot, or pivot or hinge systems previously described herein.

In use, the operating table support 304 utilizes electric or other power means to move the support section 312 up and down and at an incline, as is known in the art. The operating table support 304 can also tilt or rotate from side to side. In response to the movement of the section 312, the section 314 also moves, resulting in upward and downward breaking illustrated in FIGS. 32 and 33. In response to the movement of the section 312, the electric powered telescoping base 302 moves the pier 306 toward or away from the support 304. The pier 306 includes a motor for raising and lowering the pier at the connection 320.

As stated above with respect to other embodiments of the invention described herein, it is foreseen that cable drives as described herein, other types of drives including screw drives, hydraulic systems, and the like, may be utilized to facilitate both upward and downward breaking of the support structure 310 at the joint 316.

With reference to FIGS. 35-47, another patient support structure according to the invention, generally 401 includes first and second upright support piers or columns 403 and 404 that are connected to one another by a non-telescoping base support 402. In some embodiments according to the invention, each column may be surmounted on an independent movable or stationary base. The column 403 is connected to a first support assembly, generally 405 and the column 404 is connected to a second support assembly, generally 406. Between them, the support assemblies 405 and 406 uphold at least one removable elongate and articulate, substantially centrally jointed or breaking patent holding or support structure, generally 410. The assembly includes a first frame section 412, a second frame section 414 and a pair of identical hinge assemblies, generally 416, disposed between and connecting the first and second frame sections 412 and 414. In the illustrated embodiment, the first frame section 412 for holding a head and upper body of a patient is of a slightly shorter longitudinal length (along an axis X) than the second frame section 414. Therefore, the spaced hinge assemblies 416 are approximately centrally located relative to a body of a patient being placed on the structure 410. In the illustrated embodiment, the hinge assembly further includes a drive system that includes a pull rod assembly, generally 418, and cooperating spaced slider bars 420. Again, other drive systems are foreseen.

The columns 403 and 404 are substantially similar in form and function to the columns 3 and 4 previously described herein with respect to the structure 1. The columns 403 and 404 are supported by outwardly extending feet 422 that include casters that may be equipped with a floor-lock foot lever for lowering the feet 422 into a floor-engaging position. The columns 403 and 404 each include two or more telescoping lift arm segments respectively that permit the height of each of the columns 403 and 404 to be selectively increased and decreased in order to raise and lower all or a selected portion of the connected patient support structure 410.

Each of the support assemblies 405 and 406 generally includes a rotation subassembly 426 and 426' and an angulation subassembly 427 and 427', respectively, that are the same or substantially similar to the subassemblies 26, 26', 27 and 27' previously described herein with respect to the structure 1. In the illustrated embodiment, the angulation subassembly 427 connected to the frame 412 for holding the head and upper body of a patient is shown as substantially identical to the subassembly 27 and therefore shall not be described further herein. The subassembly 427' is substantially similar to the subassembly 27', but with some modifications, including a frame 436 disposed transverse to the overall longitudinal axis X of the structure 401, the frame 436 providing for slidable support of the pair of identical slider bars 420 that are disposed at either side of the frame 414 and near the subassembly 427'.

Similar to the rotation subassembly 26 previously described herein, the rotation subassembly or mechanism 426, includes at least one motor housing 430 surmounting the support column 403. It is foreseen that a cooperating motor may also be mounted on the support column 404. A main rotational shaft 432 extends from the motor housing 430 that turns a rotation structure or bar that in turn is connected to and rotates the patient support 410 about a longitudinal axis. In particular, the motor housing 430 contains a rotary electric motor or other actuator drivingly engaged with the shaft 432. The rotation mechanism 426 is operated by actuating the motor using a switch or other similar means. The shaft 432 rotationally cooperates with a pair of substantially vertically disposed translation posts or H-bar posts 440, the posts 440 being attached to and disposed at either end of the transverse rotation structure or bar 433. Each H-bar post 440 includes a plurality of apertures 444, allowing for selective, hinged vertical placement of the frame section 412 identical or substantially similar to what has been described previously herein with respect to the H-bar posts 40, the angulation sub-assembly 27 and the frame end section 58 of the frame section 12 previously described herein with respect to the structure 1.

Figure 38:
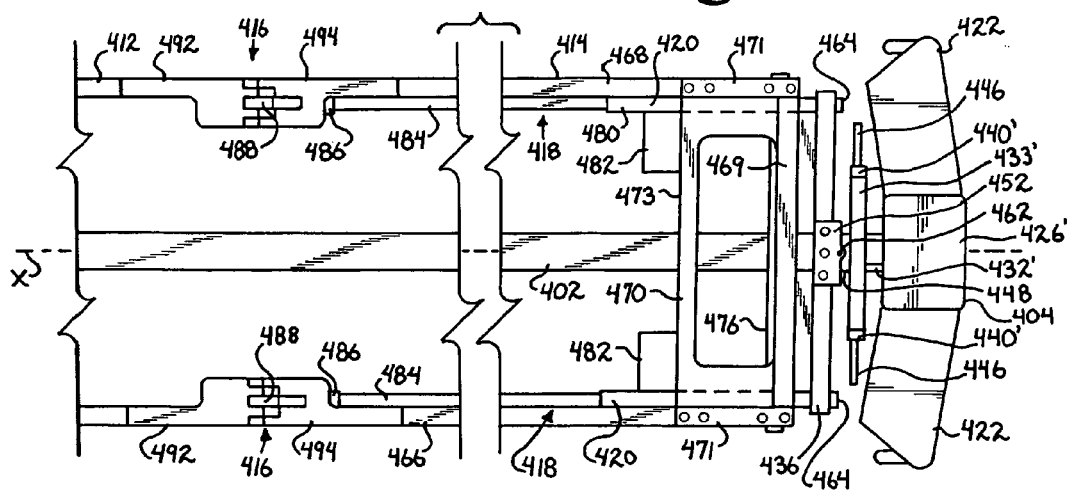
FIG. 38 is an enlarged and partial top plan view of a portion of the structure of FIG. 35 and shown in the same position as shown in FIG. 35.
Figure 40:
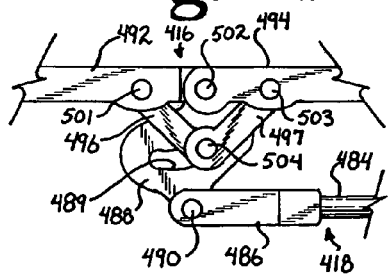
FIG. 40 is an enlarged and partial side elevational view of the structure of FIG. 35 and shown in the same position as shown in FIG. 35.
Figure 39:
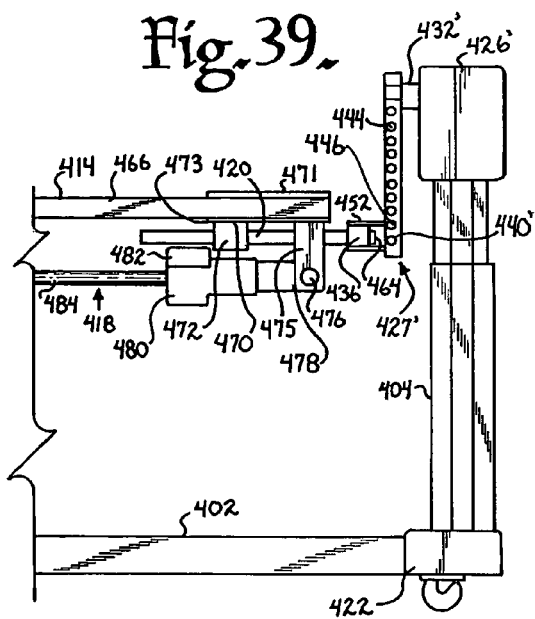
FIG. 39 is an enlarged and partial side elevational view of the structure of FIG. 35 and shown in the same position as shown in FIG. 35.

With particular reference to FIGS. 38-40, as stated above, the sub-assembly 426' is substantially similar to the sub-assembly 426 and therefore may include a motor and further includes either an active or passive rotational shaft 432' that engages a rotation structure or bar 433' that is attached to a pair of substantially vertically disposed H-bar posts 440'. A plurality of cooperating apertures 444' formed in the posts 440' provide passageway for a pivot pin 446 to extend therethrough. The pivot pin 446 is receivable in each cooperating pair of apertures 444', allowing for selective placement of a translation connector 448 that is sized and shaped to be received between the pair of posts 440' and also receive the pivot pin 446 therethrough. The pin 446 and connector 448 are thus positionable in an orientation transverse to the longitudinal axis X of the patient support frame 410 at a variety of heights to be selected by the surgeon and readily changeable, even during surgery if necessary, to vary the height of the frame section 414. The multiple location or height feature is also advantageous when more than one frame or patent structure is mounted in tandem, for example, when both a frame and imaging table are used together, such as is shown in the embodiment illustrated in FIGS. 25-29. The position of the frame or other structure may be desirably changed to provide close proximity to an imaging top with a distance between a patient support and an imaging top being expandable or reduceable depending upon the size or other attributes of a patient and surgical or other requirements. The connector 448 has a slot for receiving the pivot pin 446. It is noted that the H-bar support 440', apertures 444', elongate transverse pin 446 and translation connector 448 are the same or substantially similar in form and function with the respective support 40, apertures 44, transverse pin 46 and translation connector 48 previously described herein with respect to the structure 1.

The translation connector 448 is in turn attached to a pivot connector 452 that is substantially similar to the pivot connector 52 previously described herein with the exception that rather than being attached directly to an end piece or section of the patient support frame 414, the pivot connector 452 is fixed to the frame 436 that is fixed to and supports the slider bars 420 near end surfaces 464 thereof. Thus, the slider bars 420 are in a hinged relationship with the H-bar supports 440'. The slider bars 420 are also in slidable attachment with the frame section 414 and disposed substantially parallel to a longitudinal axis of the section 414 as will be described in greater detail below. Such slidable attachment facilitates upward and downward breaking or hinging of the section 414 with respect to the section 412 at the hinge mechanism 416. Also as more fully described below, the pull rod assembly 418, that is connected to both the frame section 414 and the hinge mechanism 416, is extendable and retractable, controlling the hinge or break angle of the patient support 410 and rendering the support 410 rigid at a desired upward or downward break or joint of the hinge mechanism 416.

With particular reference to FIGS. 38 and 39, the support frame section 414 includes opposed elongate and parallel frame sections 466 and 468 attached to one another by a transverse end frame section 469. A support plate 470 is attached to and is disposed below each of the sections 466, 468 and 469 to provide additional support and stability to the frame section 414 at and near the end section 469. Further support is provided by a pair of frame support plates 471, both of which are fixed to the end support frame section 469 near one end thereof; one plate 471 being fixed to the section 466 and the other plate 471 being fixed to the section 468. At least one pair of slider bar holding structures 472 are fixed to the support plate 470 and extend downwardly therefrom at each of the frame sections 466 and 468. Each structure 472 includes a through bore that extends parallel to the frame sections 466 and 468, the structure 472 for slidably receiving one of the slider bars 420 directly below one of the frame sections 466 and 468 and also orienting the pair of slider bars 420 in a direction substantially parallel to the frame sections 466 and 468. The illustrated slider bar holding structures 472 are spaced from the end frame section 469 and located near a forward edge 473 of the plate 470. In the illustrated embodiment, the holding structures 472 are also bolted to the frame sections 466 or 468. A pair of pull-rod supports 475 are also fixed to the support plate 470 and the frame 414 and extend downwardly therefrom at each of the frame sections 466 and 468 and also downwardly from the end frame section 469. Each structure 475 includes a through bore for receiving a transverse pivot pin or bar 476 mounted below the slider bars 420. The pull-rod assembly 418 is attached to the support 475 at the pivot pin 476 and is thus in hinged relationship with the support 475, pivotally attached thereto at end portions 478.

The pull-rod assembly 418 further includes a pair of housings 480, each housing attached to an end portion 478 and having a powered actuator 482 cooperating with one of a pair of rotatable extendible and retractable rods 484 and a pair of hinge connectors 486, each pivotally attached to a respective cam plate 488 of the respective hinge mechanism 416 at a respective pivot pin 490. The cam plate 488 has a substantially centrally located curvilinear wall 489 forming a curvate aperture or slot, a lower circular aperture for receiving the pin 490 and an upper circular aperture for receiving a pin 502, described in greater detail below. Each pull rod 484 is rotatably mounted within one of the housings 480, such rotation being controlled by operation of the actuator 482 located in the housing 480 and engaged with the rod 484 to screw and thus selectively move or draw the rod 484 into or away from the hinge mechanism 416 in a direction along a longitudinal axis of the rod 484, that in turn results in breaking or jointing of the patient support 410 at the hinge mechanism 416. It is foreseen that other embodiments according to the invention may utilize other types of push/pull rods or mechanisms, including, for example hydraulic systems. An additional centrally located pull-rod or piston may be included to provide additional support. Furthermore, other hinge mechanisms according to the invention may be utilized in lieu of the mechanism 416, for example including, but not limited to, polyaxial joints, roller with spokes, sprockets, toothed gears, universal axis gears, or the like.

With particular reference to FIG. 41, the illustrated pair of hinge mechanisms 416, each having a cam plate 488, further include a pair of forked arms 492 extending from the frame section 412 and a pair of cooperating forked arms 494 attached to and extending from the section 414. Hinge arms 496, 497, 498 and 499 having apertures near opposite ends thereof for receiving pivot pins cooperate with the respective cam plate 488 and adjacent forked arms 492 and 494 at pivot pins 501, 502, 503 and 504. All of the pivot pins 490, 501, 502, 503 and 504 are disposed transverse to the longitudinal axis X of the patient support structure 401. In particular, the pivot pin 501 is received by circular apertures located near first ends of the hinge arms 496 and 498 and a circular aperture in the arm 492, thus pivotally attaching the arm 492 with both the hinge arms 496 and 498. The pivot pin 502 is received by an upper circular aperture in the cam plate 488 and circular apertures located near the ends of each of the forked arms 492 and 494, thus pivotally attaching the cam plate 488 with both of the forked arms 492 and 494. The pivot pin 503 is received by circular apertures located near first ends of the hinge arms 497 and 499 and a circular aperture in the arm 494, thus pivotally attaching the arm 494 with both the hinge arms 497 and 499. The pivot pin 504 is received by the slot 489 and also by circular apertures located near second ends of the hinge arms 496, 497, 498 and 499, thus pivotally attaching all four hinge arms 496, 497, 498 and 499 with the cam plate 488 at the slot 489.

Also, with particular reference to FIGS. 35 and 38-41, the structure 401 is shown in a neutral, planar orientation, with the pull-rod assembly 418 holding the hinge mechanism 416 in such neutral position, with the forked arms 492 and 494 in parallel. In such position, the pin 504 is located at or near a rear-ward end of the slot 489.

Figure 42:
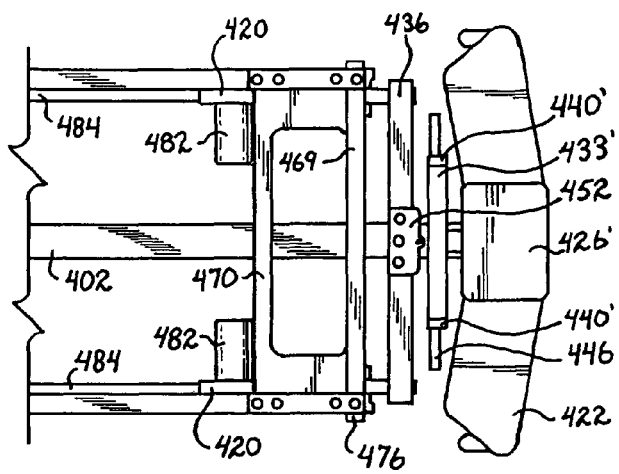
FIG. 42 is an enlarged and partial top plan view of a portion of the structure of FIG. 35 and shown in the same position as shown in FIG. 36.
Figure 44:
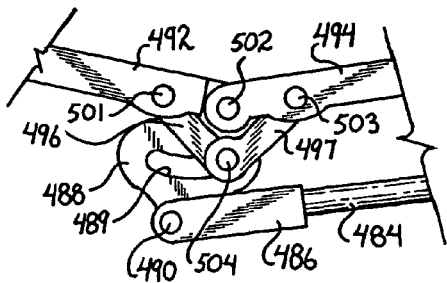
FIG. 44 is an enlarged and partial side elevational view of the structure of FIG. 35 and shown in the same position as shown in FIG. 36.
Figure 43:
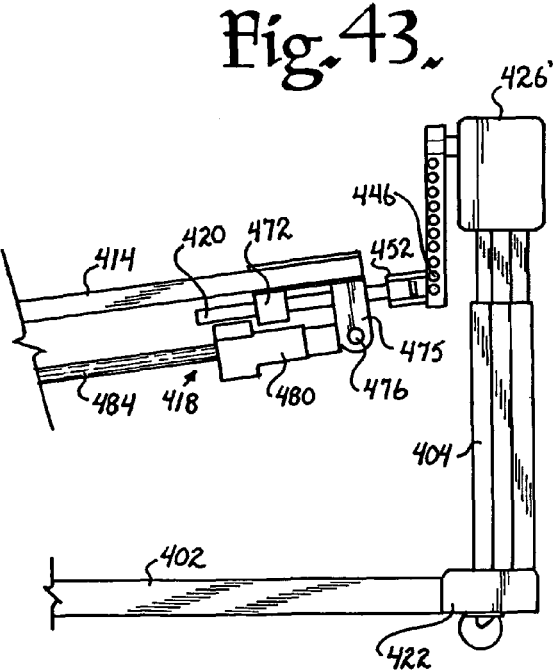
FIG. 43 is an enlarged and partial side elevational view of the structure of FIG. 35 and shown in the same position as shown in FIG. 36.
Figure 45:
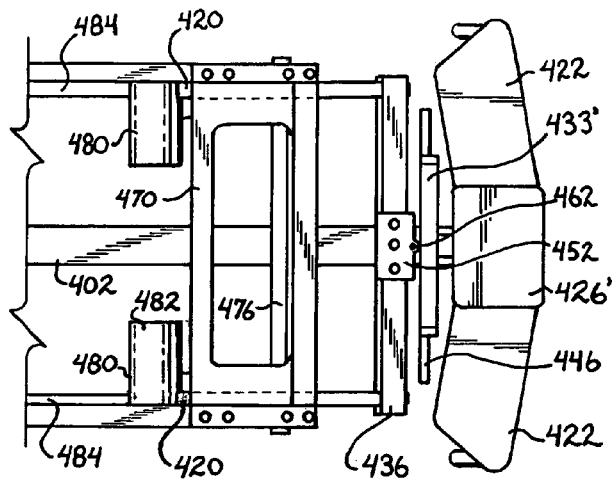
FIG. 45 is an enlarged and partial top plan view of a portion of the structure of FIG. 35 and shown in the same position as shown in FIG. 37.
Figure 47:
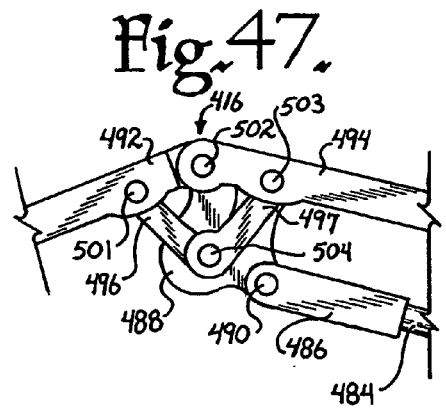
FIG. 47 is an enlarged and partial side elevational view of the structure of FIG. 35 and shown in the same position as shown in FIG. 37.
Figure 46:
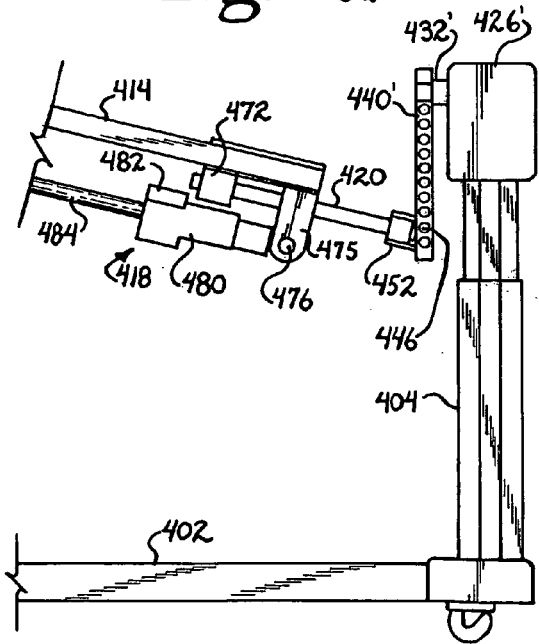
FIG. 46 is an enlarged and partial side elevational view of the structure of FIG. 35 and shown in the same position as shown in FIG. 37.

With reference to FIGS. 42-44, as the rod 484 is rotated to selectively lengthen the rod 484, the pin 504 remains near the rear-ward end of the slot 489 and the pushing of the rod toward the hinge mechanism 416 pivots the cam plate 488 at the pivot pin 490, causing the arms 492 and 494 to move toward the rod hinge connector 486 and thus pivot the patient support at the pin 502, causing a downward break or joint in the patient support 410. With reference to FIGS. 45-47, as the rod 484 is rotated to selectively shorten the length thereof, the support portion 414 slides along the slider bars 420 away from the end support 404. At the same time, the pin 504 slides along the slot 489 to an opposite or forward end thereof as the cam plate pivots in a forward direction about the pin 490. The movement of the rod 484 thus causes an upward break at the pivot pin 502. In the illustrated embodiment, the patient frame is pinned at the head end, but is free to move along the fixed slider bar 420 at the foot end, providing dynamic support to the patient frame. The slider bar mechanism can be attached to a bearing block mechanism to provide lateral translation movement, as described previously.

It is noted that since the patient frame is free to move over the slider bar, a horizontal force component is generated by the combined components of the patient support. When the support is broken or jointed upward, the angle of the foot end frame imparts a horizontal force on the slider that urges the end supports 403 and 404 toward one another. When the table is broken downward, a horizontal force develops that tends to push the end supports apart. It has been found that the magnitude of the horizontal force is a function of support loading and break angle, and thus, for example, if a working limit of five hundred pounds is selected for the patient support, a worst case of horizontal loading is only about fifty-eight pounds at an upward break or joint of thirty-five degrees. It is noted that the illustrated structure 401 advantageously supports a breaking or jointing range from about thirty-five degrees up to about twenty degrees down. Throughout such range, the horizontal forces imposed by the structure are minimized by the illustrated locked support frame that moves on a slider bar at the foot end of the support.

As with the structure 1 configurations illustrated in FIGS. 18-23, the upward and downward breaking of the patient support 410 may be modified by placing the portions 412 and 414 at different vertical locations along the H-bar supports 440 and 440', thus resulting in symmetrical or asymmetrical breaking configurations. Furthermore, the portions 412 and 414 may be rotated or tilted as described above with respect to the structure 1.

It is to be understood that while certain forms of the present invention have been illustrated and described herein, it is not to be limited to the specific forms or arrangement of parts described and shown.

What is claimed and desired to be secured by Letters Patent is as follows:

1. An apparatus for supporting a patient during a medical procedure, the apparatus comprising:
   a) a selectively telescoping support subassembly including first and second spaced opposed upright end supports; each end support being attached to a base structure;
   b) an elongate patient support subassembly extending between the first and second end supports and held by the end supports in spaced relation with respect to a floor, the patient support subassembly having pivotally connected head and foot end portions alignable in a first plane and movable to a plurality of angular orientations with respect to one another on either side of the first plane;
   c) an articulation in the patient support subassembly between the head and foot end portions and movable to a plurality of angular orientations associated with the angular orientations of the head and foot end pivotally connected portions;
   d) a translation connector subassembly cooperating with the articulation and pivotally connected head and foot end portions so as to allow the patient support subassembly to move through the various angular orientations thereof without the end supports moving relative to each other; and
   e) a powered actuator.

2. The apparatus of claim 1 wherein one of the first and second upright end supports is in cantilevered relationship with respect to one of the head and foot end portions.

3. The apparatus of claim 1 wherein the translation connector subassembly comprises a pull-rod.

4. The apparatus of claim 3 wherein the pull-rod is attached to the foot end portion.

5. The apparatus of claim 3 wherein the translation connector subassembly further comprises at least one slider bar, slidably attached to one of the head and foot end portions, the slider bar pivotally attached to one of the upright end supports.

6. The apparatus of claim 1 wherein at least one of the upright end supports further comprises a rotation mechanism.

7. The apparatus of claim 1 wherein the elongate patient support subassembly is a frame and further comprising a second patient structure, the second patient structure being an imaging table.

8. The apparatus of claim 1 wherein the patient support subassembly is detachable and placable at either end in a plurality of locations vertically spaced from the floor.

9. The apparatus of claim 1 wherein the articulation has a hinge mechanism that cooperates with the angulation subassembly.

10. The apparatus of claim 1 wherein the powered actuator is associated with the rotation and angulation subassemblies.

11. The apparatus of claim 1 further including:
    a) a patient compression structure fixedly supported between the first and second upright end supports and held in spaced relation with respect to the elongate patient support subassembly; and wherein:
    b) the orientation subassembly includes an adjustable separation subassembly operable to independently raise and lower the elongate patient support subassembly for allowing infinite adjustment of the patient support subassembly relative to the patient compression structure.

12. The apparatus of claim 11 wherein the patient compression structure includes a riser joining the patient compression structure with the orientation subassembly.

13. The apparatus of claim 12 wherein the riser includes structure for incremental adjustment of a height of the patient compression structure relative to the orientation subassembly.

14. The apparatus of claim 11 wherein the separation subassembly includes a hydraulic lift subassembly.

15. The apparatus of claim 11 wherein the separation subassembly includes a screw lift subassembly.

16. The apparatus of claim 11 wherein the separation subassembly includes a rack and pinion gear lift subassembly.

17. An apparatus for supporting a patient during a medical procedure, the apparatus comprising:
    a) first and second spaced opposed upright supports;
    b) an elongate first patient support subassembly extending between the first and second upright supports and held by the upright supports in spaced relation with respect to a floor, the first patient support subassembly having head and foot end portions alignable in a first plane and movable to a plurality of angular orientations with respect to one another on either side of the first plane;
    c) a translation connector subassembly joining at least one of the head and foot end portions with a respective upright support and including an infinitely movable separation subassembly adapted for non-incremental upward and downward movement of at least a portion of the first patient support subassembly relative to a top of the respective upright support; and
    d) an elongate second patient support subassembly removably attachable with and extending between the first and second upright supports and held in spaced relation with respect to the translation connector subassembly; and wherein
    e) the separation subassembly is operable to non-incrementally move at least a portion of the first patient support structure relative to an attached-second patient support subassembly so as to non-allow non incremental adjustment of a distance therebetween.

18. The apparatus of claim 17 wherein the orientation subassembly further includes:
   a) a rotation subassembly for rotating at least a portion of the first and second patient support assemblies;
   b) an angulation subassembly for articulating at least a portion of the first patient support subassembly so as to allow the first patient support subassembly to move through the various angular orientations thereof without the end supports moving relative to each other.

19. The apparatus of claim 18 wherein the rotation subassembly includes structure for simultaneously rotating the first and second patient support structures without changing a distance therebetween.

20. The apparatus of claim 18 wherein the second patient support subassembly includes a riser removably joining the second elongate patient support subassembly with the rotation subassembly.

21. The apparatus of claim 20 wherein the riser includes an incrementally adjustable holding structure adapted for selectively increasing and decreasing a distance between the second patient support assembly and the rotation subassembly.

22. The apparatus of claim 17 further comprising a hinge structure joining the head and foot end portions of the first patient support subassembly and cooperating with the angulation subassembly so as to allow articulation of the head and foot end portions with respect to one another.

23. The apparatus of claim 17 wherein the head and foot end portions of the first patient support subassembly are not joined so as to be independently movable.

24. The apparatus of claim 17 wherein the separation subassembly includes a hydraulic lift subassembly.

25. The apparatus of claim 17 wherein the separation subassembly includes a screw lift subassembly.

26. The apparatus of claim 17 wherein the separation subassembly includes a rack and pinion gear lift subassembly.

27. The apparatus of claim 17 wherein each of the upright supports includes structure operable to continuously increase and decrease a distance between the first patient support subassembly and the floor.

28. An apparatus for supporting a patient during a medical procedure, the apparatus comprising:
   a) an elongate first patient support subassembly held in spaced relation with respect to a floor by opposed end supports;
   b) an elongate second patient support subassembly removably joined in spaced relation with the first patient support subassembly;
   c) an orientation subassembly including:
      i) a rotation subassembly for rotating the first and second patient support assemblies;
      ii) an angulation subassembly for articulating at least a portion of the first patient support subassembly so as to allow the first patient support structure to move through the various angular orientations thereof without the end supports moving relative to each other; and
      iii) a continuously movable separation subassembly adapted for upward and downward movement over an infinitely adjustable range between the first patient support structure relative to the rotation subassembly so as to non-incrementally increase and decrease a space between the first and second patient support subassemblies.

29. The apparatus of claim 28 wherein the first patient support subassembly includes head and foot end portions alignable in a first plane and movable to a plurality of angular orientations with respect to one another on either side of the first plane.

30. The apparatus of claim 28 wherein the second patient support subassembly includes head and foot end portions.

31. The apparatus of claim 28 wherein the second elongate patient support subassembly includes a riser releasably joining the second elongate patient support subassembly with the rotation subassembly.

32. The apparatus of claim 28 the first patient support subassembly including head and foot end portions joined by a hinge structure; the hinge structure cooperating with the angulation subassembly so as to articulate the head and foot end portions with respect to one another.

33. The apparatus of claim 28 wherein first patient support subassembly includes non-joined and independently movable head and foot end portions.

34. The apparatus of claim 28 wherein the separation subassembly includes a hydraulic lift subassembly.

35. The apparatus of claim 28 wherein the separation subassembly includes a screw lift subassembly.

36. The apparatus of claim 28 wherein the separation subassembly includes a rack and pinion gear lift subassembly.

37. The apparatus of claim 28 wherein each of the end supports includes structure operable to continuously increase and decrease a distance between the first patient support subassembly and the floor.

38. An apparatus for supporting a patient during a medical procedure, the apparatus comprising:
   a) a rotation subassembly held in spaced relation with respect to a floor by an upright end structure;
   b) an elongate primary patient support subassembly rotatably joined with the rotation subassembly at a first end, the primary patient support subassembly having head and foot end portions alignable in a first plane and movable to a plurality of angular orientations with respect to one another on either side of the first plane;
   c) an elongate secondary patient support subassembly removably held in spaced relation with respect to the rotation subassembly; and
   d) a separation subassembly adapted for upward and downward movement of at least a portion of the primary patient support subassembly relative to the secondary patient support subassembly over a continuous range so as to non-incrementally increase and decrease a distance therebetween.

39. The apparatus of claim 38 including a hinge structure pivotably joining the head and foot end portions.

40. The apparatus of claim 38 wherein the upright end support is joined with the head end portion and including a second upright end support rotatably joined with the foot end portion, the head and foot end portions not being joined so as to be independently movable.

41. The apparatus of claim 38 wherein the separation subassembly includes a hydraulic lift subassembly.

42. The apparatus of claim 38 wherein the separation subassembly includes a screw lift subassembly.

43. The apparatus of claim 38 wherein the separation subassembly includes a rack and pinion gear lift subassembly.

44. The apparatus of claim 38 wherein the primary patient support subassembly is adapted for 360° rotation with respect to at least one of the end supports.

45. The apparatus of claim 38 wherein the upright pier includes structure operable to increase and decrease a distance between the primary patient support subassembly and the floor over a continuous range.

46. The apparatus of claim 38 including an articulation subassembly operable to articulate at least a portion of the first patient support subassembly, so as to align the head and foot end portions in the first plane and to move the head and foot end portions to a plurality of angular orientations with respect to one another on either side of the first plane.

47. An apparatus for supporting a patient during a medical procedure; the apparatus comprising:
 a) first and second end supports;
 b) an elongate patient support structure extending between and being supported by the first and second end supports; wherein
 c) the patient support structure includes a frame section that has spaced opposite sides, so as to provide an open space therebetween that is free of obstructions and that allows a patient's belly to extend downward between the opposite sides when a patient is in a prone position on the patient support structure; and wherein
 d) the frame section is a first frame section and including a second frame section joined with the first frame section at an articulation.

48. An apparatus for supporting a patient during a medical procedure, the apparatus comprising:
 a) first and second opposed end supports;
 b) a patient support structure connected to and bridging substantially between the first and second end supports, the support structure having a first portion and a second portion, the first and second portions being selectively lockable in a first substantially planar orientation along a longitudinal axis of the support structure, the first and second portions also being selectively positionable and lockable in a plurality of angles with respect to one another, with each portion movable to a position on either side of the first planar orientation; and
 c) a translation connector joining at least one end of the patient support structure to a respective end support so as to allow the patient support structure to be moved between any of the plurality of angles with respect to one another without the end supports moving relative to each other; the translation connector including a slider bar joined to a first of the patient support structure and the first end support and a slider bar holder structure joined to a second of the patient support structure and the first end support; the slider bar being aligned to slide relative to the slider bar holder structure to allow the patient support structure to move away from and toward the first end support when the configuration of the patient support structure changes.

49. An apparatus for supporting a patient during a medical procedure, the apparatus comprising:
 a) a support subassembly including first and second spaced opposed upright end supports; each end support being attached to a respective base structure; at least one of the first and second end supports being vertically height adjustable;
 b) an elongate patient support with first and second ends and extending between the first and second end supports; the patient support being held by the end supports in spaced relation with respect to a floor, the patient support connected to and supported between the end supports; the patient support having a single breaking location spaced from the end supports and adapted to interact with the patient when the patient is located on the patient support; and
 c) a vertical elevator connecting a patient support first end with a respective end support; the vertical elevator being controllable to allow infinite adjustment of the support first end relative to the respective end support so as to align and orient the patient support subassembly; and wherein
 d) the patient support is controllable to be upwardly and downwardly articulatable at both the first and second ends of the patient support relative to respective end supports and at the breaking location so as to be adapted to manipulate a patient into a plurality of selectively prone and non-prone positions in cooperation with an end support translation compensation mechanism, while also cooperating with the end supports to move the patient between vertical positions.

50. The apparatus according to claim 49 including:
 a) a second vertical elevator connecting the second end of the patient support to a respective end support.

51. The apparatus of claim 49 wherein one of the first and second end supports is in cantilevered relationship with respect to an end portion of the elongate patient support.

52. The apparatus of claim 49 further including:
 a) a patient compression structure fixedly supported between the first and second end supports and held in spaced relation with respect to the patient support; and
 b) an adjustable separation subassembly operable to independently raise and lower the patient support for allowing infinite adjustment of the patient support relative to the patient compression structure.

* * * * *